(12) United States Patent
Dukler et al.

(10) Patent No.: US 11,480,569 B2
(45) Date of Patent: Oct. 25, 2022

(54) BIOMARKER TEST AND METHOD FOR ASSESSING MUCOSAL HEALING IN RESPONSE TO TREATMENT OF ULCERATIVE COLITIS

(71) Applicants: KEPLER DIAGNOSTICS, INC., Simi Valley, CA (US); KATHOLIEKE UNIVERSITEIT LEUVEN, Leuven (BE)

(72) Inventors: Avinoam Dukler, Newbury Park, CA (US); Randy Ringold, Simi Valley, CA (US); Severine Vermeire, Leuven (BE); Magali De Bruyn, Leuven (BE); Ghislain Opdenakker, Leuven (BE)

(73) Assignees: Glycominds, LLC, Simi Valley, GA (US); Katholieke Universiteit Leuven, Leuven (BE)

( * ) Notice: Subject to any disclaimer, the term of this patent is extended or adjusted under 35 U.S.C. 154(b) by 585 days.

(21) Appl. No.: 16/463,835

(22) PCT Filed: Nov. 30, 2017

(86) PCT No.: PCT/US2017/064029
§ 371 (c)(1),
(2) Date: May 23, 2019

(87) PCT Pub. No.: WO2018/102591
PCT Pub. Date: Jun. 7, 2018

(65) Prior Publication Data
US 2019/0331679 A1    Oct. 31, 2019

Related U.S. Application Data

(60) Provisional application No. 62/457,139, filed on Feb. 9, 2017, provisional application No. 62/429,069, filed on Dec. 1, 2016.

(51) Int. Cl.
| | |
|---|---|
| *G01N 33/564* | (2006.01) |
| *G01N 33/53* | (2006.01) |
| *G01N 33/74* | (2006.01) |
| *G01N 33/68* | (2006.01) |
| *G01N 33/569* | (2006.01) |
| *G16H 50/30* | (2018.01) |

(52) U.S. Cl.
CPC ........... *G01N 33/564* (2013.01); *G01N 33/53* (2013.01); *G01N 33/56972* (2013.01); *G01N 33/68* (2013.01); *G01N 33/74* (2013.01); *G01N 2333/4737* (2013.01); *G01N 2800/065* (2013.01); *G01N 2800/52* (2013.01); *G16H 50/30* (2018.01)

(58) Field of Classification Search
CPC ................. G01N 33/564; G01N 33/53; G01N 33/56972; G01N 33/68; G01N 2333/4737; G01N 2800/065; G01N 2800/52
See application file for complete search history.

(56) References Cited

PUBLICATIONS

Fournier et al. The role of neutrophils during intestinal inflammation. Mucosal Immunology 5 (4): 354-366 (Jul. 2012).*
Fengming et al. Disease Markers. Hindawi. vol. 2014, Article ID 710915. pp. 1-12 (May 19, 2014).*
Sun et al. The Roles of Cathelicidin LL-37 in Inflammatory Bowel Disease. Inflamm Bowel Disease. 22 (8): 1986-1991 (Aug. 2016).*

* cited by examiner

*Primary Examiner* — Gailene Gabel
(74) *Attorney, Agent, or Firm* — Karim Lagobi

(57) ABSTRACT

Mucosal healing is an indication to the disease activity level in patients affected by inflammatory bowel diseases, and it is thus far mainly monitored by endoscopy. Instead or in addition to endoscopy, the invention provides blood test using biomarkers and an index that allows a practitioner to assess the status of mucosal healing, to change or adapt dosage of treatment and to predict which patient will become responder versus non-responder to treatment as assessed by endoscopy. While none of neutrophils cell count, c-reactive protein (CRP), Human type of Cathelicidin (LL-37), or Chitinase 3-like 1 (CHI3L1) alone is able to provide an assessment means of mucosal healing, the invention provides a novel combination of the levels of these biomarkers to assess the level of mucosal healing in relation to endoscopic healing.

17 Claims, 14 Drawing Sheets

BIOMARKER TEST AND METHOD FOR ASSESSING MUCOSAL HEALING IN RESPONSE TO TREATMENT OF ULCERATIVE COLITIS

CROSS REFERENCE TO RELATED PATENT APPLICATIONS

The present application is a national phase of international (PCT) application number PCT/US2017/064029, filed on Nov. 30, 2017, that claims priority to U.S. provisional patent applications No. 62/429,069, filed on Dec. 1, 2016, and provisional patent application No. 62/457,139, filed on Feb. 9, 2017, the content of each of which is included herein by reference.

FIELD OF THE INVENTION

The invention relates to methods and apparatus for assessing mucosal healing in response to treatment of inflammatory bowel diseases; more specifically, the invention is a multi-immune pathway test panel and method using a set of biomarker levels to assess mucosal healing as a response to treatment of ulcerative colitis, which allows a medical practitioner to predict the status of mucosal healing.

BACKGROUND OF THE INVENTION

Inflammatory bowel disease (IBD), including Crohn's disease and ulcerative colitis, are chronic relapsing diseases that lead to structural damage and destruction of the bowel wall. Ulcerative colitis, for example, is a chronic relapsing disease manifested as an inflammation of the colon. While the cause of Ulcerative colitis is not known, the disease is suspected to be triggered by environmental factors, and susceptibility to the disease is presumed to have a genetic component.

Ulcerative colitis symptoms vary in severity and frequency and include frequent stools, diarrhea, blood in stool, abdominal pain, fever, weight loss and anemia. Ulcerative colitis patients may also experience extra intestinal manifestations such as arthritis and dermatological or ocular manifestations. In addition, patients have a significant elevated risk of developing colon cancer.

There exists no known cure for ulcerative colitis, and most patients require life-long treatment with medication to mitigate the symptoms, and hopefully prevent or postpone surgery. The goal of treatment is to induce remission (diminishing of symptoms or symptom free). If achieved, this is followed by the administration of maintenance medications to prevent a relapse of the disease.

Standard treatment for ulcerative colitis depends on the extent of colon involvement and disease severity and includes anti-inflammatory drugs, immunosuppressive drugs, as well as biological therapies targeting specific components of the immune response. For patients with chronic active disease not responding to medical therapy, colectomy is often the only remaining option.

A lack of universal response to current therapies, the risks of infection and neoplasia, a requirement for parenteral administration, and the development of antidrug antibodies have created a need for tools to identify responders versus non-responders.

Several data prove the capacity of both oral and rectal aminosalicylates to induce MH in mild to moderately active UC. For example, in the case of topical 5-aminosalicylic acid (5-ASA), a meta-analysis of 10 studies showed that 36% of patients receiving topical 5-ASA for two to six weeks achieved endoscopic remission compared to 17% of patients receiving placebo (Marshall et. al. Gut 1997; 40:775-81). As far as oral 5-ASA is concerned, the percentage of endoscopic remission reported in several studies ranges from 25% to 70%, although different 5-ASA doses and formulations, different definitions of MH, and different time points of endoscopic evaluation have been used (Green et. al. Alimentary Pharmacology and Therapeutics 2002; 16:61-8; Kruis et. al. Gut 2009; 58:233-40; Vecchi et. al. Alimentary Pharmacology and Therapeutics 2001; 15:251-6). In a recent meta-analysis involving 3977 patients treated with oral 5-ASA and 2513 patients treated with rectal 5-ASA, the overall rate of MH was 36.9% in patients receiving oral 5-ASA and 50.3% in patients receiving rectal 5-ASA (RÖmkens et. al. Inflammatory Bowel Diseases 2012; 18:2190-8).

A randomized controlled trial (RCT) published in 2006 by Ardizzone et al. compared Azathioprine (AZA) with 5-ASA for the treatment of steroid-dependent UC. On intention-to-treat analysis, AZA induced clinical and endoscopic remission in 55% of patients compared to 19% in those using 5-ASA. The per protocol analysis revealed that AZA induced MH in almost 60% of patients compared to 20% for 5-ASA. Endoscopic remission was defined as a Baron index 1 or 0. Data on another immunomodulator methotrexate (MTX) are more limited but an open label study with different MTX doses, and different treatment duration reported a percentage of MH of approximately 60% in ulcerative colitis (Paoluzi et. al. Alimentary Pharmacology and Therapeutics 2002; 16:1751-9).

Corticosteroids are not powerful in inducing MH in Ulcerative Colitis, despite having excellent capacity to induce clinical remission in Crohn's Disease. An important historical trial, published by Truelove et al. in 1955 (British Medical Journal 1955; 2:1041-8), showed that steroids were capable of inducing normalization or improvement of the endoscopic findings. Endoscopic remission was reached in 30% of patients receiving steroids vs 10% of patients receiving placebo (p=0.02); endoscopic improvement was observed in 22% vs 21% of patients, respectively, and no change or worsening of endoscopic findings was found in 48% vs 68% of patients, respectively. More recently, a prospective trial conducted by Ardizzone et al. (Clinical Gastroenterology and Hepatology 2011; 9:483-9) on 157 ulcerative colitis patients at their first steroid course showed that approximately 35% of patients achieved both clinical and endoscopic remission, 25% of patients achieved clinical but not endoscopic remission, while another 35% of patients failed to respond to steroids.

In the last 19 years, the advent of anti-TNF($\alpha$) agents, such as infliximab (IFX) (REMICADE®) and adalimumab (ADA) (HUMIRA®) as wells as certolizumab (CIMZIA®), golimumab (SIMPONI®)) has offered new options in the management of Ulcerative Colitis. Data available from different sources (subgroup analysis of RCTs, observational cohort studies, and, more recently, RCTs) that have considered MH as primary or secondary end point, show that anti-TNF($\alpha$) therapies can induce rapid and sustained MH. Recently variations of biosimilars to infliximab such as INFLECTRA® (infliximab-dyyb) were approved by the United States Food and Drug Administration and The European Commission—FLIXABI®. Table 1 (below) summarizes the results of the rate of mucosal healing in response to anti-TNF($\alpha$) drugs in Ulcerative Colitis, as carried in the following published studies (in Table 1 each study is specifically referenced as follows):

Rutgeerts: Rutgeerts, 2005 ACT 1, ACT 2; Panaccione: Panaccione, 2011 ulcerative colitis Success TRIAL; Reinisch: Reinisch, 2011; and Sanborn: Sanborn, 2012.

TABLE 1

| Study Ref. | No. of Patients Moderate to Severe UC | Treatment Regimen | Definition of MH | Treatment Time | % MH |
|---|---|---|---|---|---|
| Rutgeerts | 728 | Scheduled IFX 5 or 10 mg/kg every 8 weeks Placebo 54 weeks (ACT 1) 30 weeks (ACT 2) | Mayo Endoscopic subscore ≤ 1 | Week 8 Week 30 Week 54 | 60.7% IFX 32.3% Placebo 50.6% IFX 27.4% Placebo 46.0% IFX 18.2% Placebo |
| Panaccione | 239 | AZA 2.5 mg/kg IFX 5 mg/kg IFX 5 mg/kg + AZA 2.5 mg/kg 16 weeks | Mayo Endoscopic subscore ≤ 1 | Week 16 | 37% AZA 55% IFX 63% AZA + IFX |
| Reinisch | 390 | ADA 160/80 mg or 80/40 mg at weeks 0 and 2 followed by 40 mg at weeks 4 and 6 Placebo 8 weeks | Mayo Endoscopic subscore ≤ 1 | Week 8 160/80 80/40 | 46.9% ADA 37.7% ADA 41.5% Placebo |
| Sanborn | 494 | ADA 160/80 and then 40 mg eow Placebo 52 weeks | Mayo Endoscopic subscore ≤ 1 | Week 8 week 52 | 41.1% ADA 31.7% Placebo 25.0% ADA 15.4% Placebo |

In summary, about 20% to 40% of patients included in clinical trials for all TNF(α) antagonists do not show clinical response to therapy including 10% to 30% of patients that do not respond to the initial treatment and 23% to 46% of patients that lose response over time (Roda et. al., Clinical and Translational Gastroenterology (2016) 7,1-5).

Vedolizumab (ENTYVIO®), a monoclonal antibody to the α4β7 integrin, inhibits gut lymphocyte trafficking and has been demonstrated to be an effective and safe agent for the treatment of both Crohn's disease and ulcerative colitis. Study results from GEMINI I, a placebo-controlled induction and maintenance study in patients with UC, showed that vedolizumab met primary endpoints of improvement in clinical response (reduction in the Mayo Clinic score of 3 points or greater and 30 percent from baseline or greater, along with a decrease of at least 1 point on the rectal bleeding subscale or an absolute rectal bleeding score of 0 or 1) at six weeks and clinical remission (Mayo score of 2 or lower and no subscore higher than 1) at 52 weeks. In addition, a significantly greater proportion of patients receiving vedolizumab achieved mucosal healing (Mayo endoscopic subscore of 0 or 1) at 6 and 52 weeks, and glucocorticoid-free remission at 52 weeks, compared with placebo (Feagan et. al. N Engl J Med. 2013; 369; 8:699-710).

Due to the high non-responders among Ulcerative Colitis patients either in initial therapy or lost of response over time, many novel agents with different mechanism of actions are under development. Data from Phase II and Phase III studies demonstrated that each of these new agents, including: Risankizumab an inhibitor of IL-23 showed in Crohn's Disease phase II study a proof of concept in achieving mucosal healing and now is planned to test it further in Ulcerative Colitis patients. Ustekinumab which is a human IgG1 K monoclonal antibody that binds with specificity to the p40 protein subunit used by both the IL-12 and IL-23 cytokines and showed in Phase II study high efficacy in achieving mucosal healing in Ulcerative Colitis patients, is now investigated for its safety and efficacy moderate-to-severe Ulcerative Colitis patients phase III study. Filgoinib, a selective JAK1 inhibitor showed clinical remission and mucosal healing in Crohn's Disease phase II study is analyzed now also in Ulcerative Colitis patients. XELJANZ® (tofacitinib citrate, Janus kinase (JAK) inhibitor) has being investigated in phase III in patients with moderately to severely active Ulcerative Colitis and found to be safe and effective by achieving clinical remission and mucosal healing end points. Cobitolimod is a DNA-based ImmunoModulatory Sequence (DIMS) that is administered locally inside the large intestine, where it binds to the receptor Toll-like receptor 9 (TLR9) present inside immune cells as well as on the surface of epithelial cells. Recent data showed that Cobitolimod achieved clinical remission in naïve and non-responders to Anti-TNF(α) moderate to severe Ulcerative Colitis patients. Further investigation with mucosal healing is under investigation. Ozanimod is a new oral S1P1-receptor and S1P5-receptor modulator with no activity on S1P2, S1P3, and S1P4 (Cohen et. al. Lancet Neurol 2016; 15:373-81). In a phase II study Ozanimod showed clinical response and mucosal healing at week 8 (Sandborn et. al. N Engl J Med 2016; 374:1754-1762).

To date, the goal of any therapeutic treatment of IBD should be mucosal healing (MH), as it is associated with sustained clinical remission, reduced rates of hospitalization and operations as well as a lower incidence of colorectal cancer. The presence of Mucosal healing one year after the diagnosis of IBD has been shown to predict a significant reduction in surgery rates in the subsequent years. The definition of mucosal healing remains debated, but is mostly defined as the disappearance of ulceration. One of the most usable index in clinical practice is the Mayo Score. The Mayo Score is a composite of subscores from four categories, including stool frequency, rectal bleeding, findings of flexible proctosigmoidoscopy or colonoscopy, and physician's global assessment, with a total score ranging from 0-12. Within the endoscopic component of the Mayo Score, a score of 0 is given for normal mucosa or inactive UC, while a score of 1 is given for mild disease with evidence of mild friability, reduced vascular pattern, and mucosal erythema. A score of 2 is indicative of moderate disease with friability, erosions, complete loss of vascular pattern, and significant erythema, and a score of 3 indicates ulceration and spontaneous bleeding. Mucosal healing has been defined as a Mayo endoscopic subscore (MES) of 0 or 1 in major trials of biological therapies.

To monitor IBD and check the achievement of mucosal healing during a therapeutic treatment, repeated colonoscopies are needed, which puts a significant burden on the patients and presents potential risks. Physicians administering IBD treatments need alternative non-invasive approaches to monitoring and following patients under treatment or those suspected of having IBD.

In the prior art, no controlled study has been designed to identify possible predictors or surrogate markers of mucosal healing. Some clinical characteristics such as extensive disease, young age at diagnosis, and smoking status may be predictive of a more aggressive clinical course and, presumably, of a reduced clinical response to therapy as can be shown through endoscopic monitoring. Changes and normalization of C-reactive protein and fecal calprotectin may be considered as potential tools to predict treatment outcomes, guide the timing for endoscopic evaluation and possibly reduce (or replace) the need of endoscopic evaluation in assessing mucosal healing. However, as these biomarkers are negative in at least 50% of ulcerative colitis patients repeated colonoscopies are still currently needed and no method or test is available to monitor IBD and check the achievement of mucosal healing during a therapeutic treatment.

Therefore, there is a need for non-invasive methods and systems for monitoring patient to determine progress of mucosal healing.

SUMMARY OF THE INVENTION

The invention provides practitioners administering therapeutic treatment to patients affected by Inflammatory Bowel Diseases (IBD) with tools to assess the response of the patient to treatment. Mucosal healing assessment is relied upon in assessing the response to treatment, since mucosal healing is shown to be associated with sustained clinical remission, reduced rates of hospitalization and operations as well as a lower incidence of colorectal cancer. The definition of mucosal healing for this invention is bowels' healing from ulceration regardless of method of detection. Assessing mucosal healing, however, according to prior art, relies on repeated endoscopies/colonoscopie and has been defined as a Mayo endoscopic subscore (MES) of 0 or 1. To monitor IBD and check the achievement of mucosal healing during a therapeutic treatment, repeated colonoscopies are needed, which puts a significant burden on the patients and presents potential risks. Physicians administering IBD treatments need alternative non-invasive approaches to monitoring and following patients under treatment or those suspected of having IBD.

The invention provides a test panel of biomarkers which can be measured in a blood sample. The biomarker panel comprises Neutrophils count in the blood (Neutrophils), LL-37, the only cathelicidin-derived antimicrobial peptide found in humans (LL-37), Chitinase 3-like 1 (CHI3L1) and C-reactive protein (CRP). Although each of Neutrophils, LL-37, CHI3L1 and CRP, in addition to NGAL-MMP-9, provide valuable dataset for Ulcerative Colitis mucosal healing analysis when compared to MES, the sensitivity for each biomarker covers less than 50% of the ulcerative colitis patients.

The invention is a novel and powerful non-invasive biomarker method that evaluates mucosal healing using a blood-work as compared with endoscopic measurement of the response to treatment by a subject affected by ulcerative colitis. The invention provides a simple index that allows a practitioner administering a treatment to obtain the index, store data, share and compare the data among and between several institutions (e.g., hospitals and/or clinics).

Moreover, the index according to the invention is shown to closely reflect the changes in the Mayo endoscopic subscore for patients undergoing endscopic monitoring. The UCRI of the invention is therefore a powerful tool that informs a practitioner of the status of mucosal healing using the biomarker-based method of the invention.

The benefits of implementations of the invention are numerous. The invention will improve clinical practice by enabling physicians to make decisions to switch treatment earlier for UC patients who fail to achieve healing with their first treatment choice, thus reducing the number of flares and hospitalizations that occur when waiting for endoscopic evaluations. The invention also resolves the problem of determining a predictor for determining those subjects that respond to treatment versus those that do not or respond at a lesser level. Additionally, the invention allows for weighting a subject therapeutic time windows, which has never been addressed using a multi-biomarker test.

Embodiments of the invention may be utilized in Ulcerative Colitis patients as a surrogate marker for mucosal healing.

DETAILED DESCRIPTION

Figure 1:
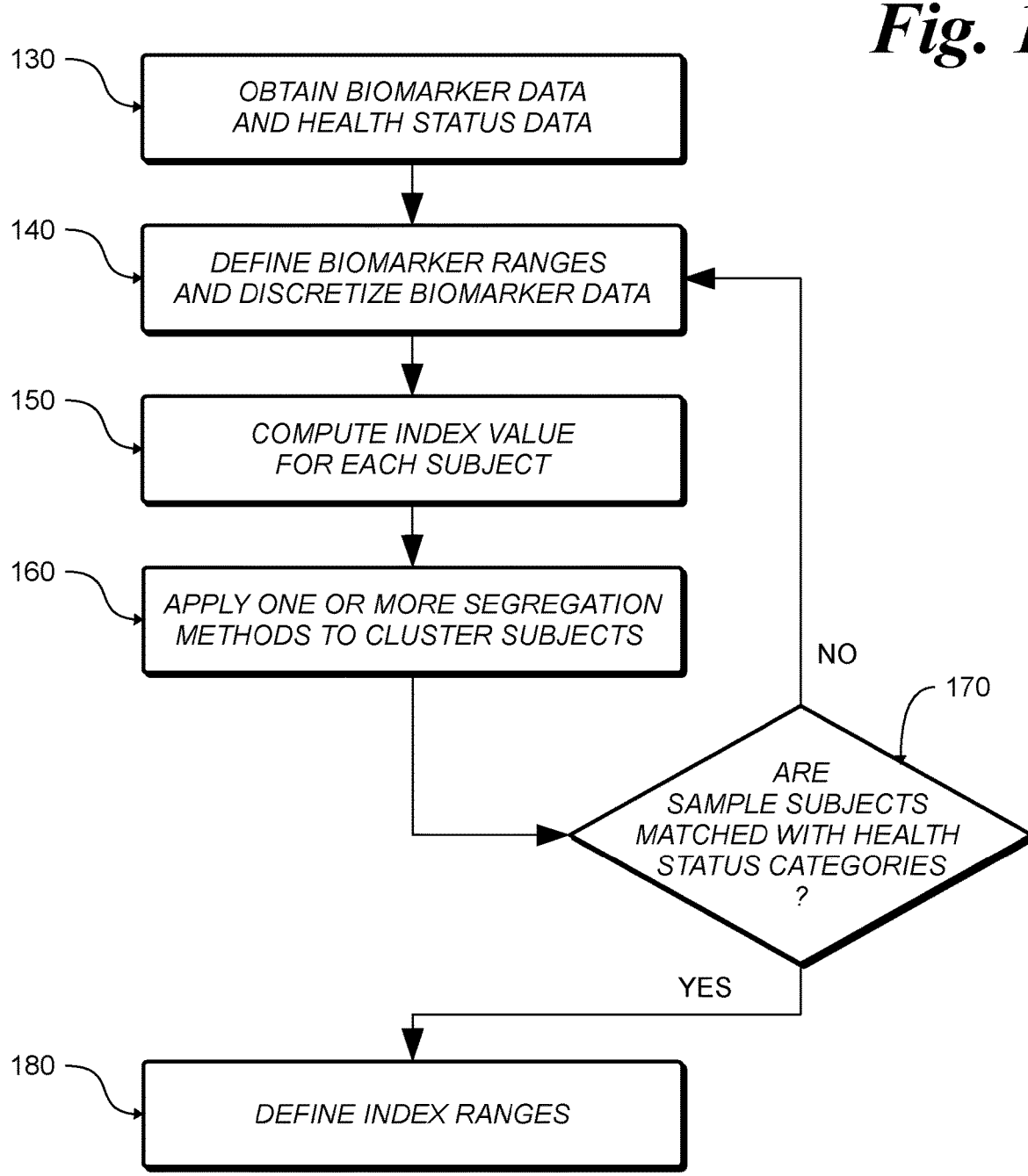
FIG. 1 is a flowchart diagram representing steps involved in developing a non-invasive method for assessing mucosal healing in subjects undergoing treatment for ulcerative colitis, in accordance with an embodiment of the invention.

The invention is a method and system for determining the level of mucosal healing and represents a non-invasive substitute for endoscopic examination for evaluation of mucosal healing. The method and system according to the invention enable a physician administering an IBD treatment to utilize blood test or kits according to the invention, to measure the level of a specific set of biomarkers in a blood and fecal samples from a patient, combine the level of the biomarkers according to the methods taught by the invention and determine mucosal healing in the patient under consideration.

To achieve the maximum therapeutic benefit for individual subjects, it is important to be able to specifically quantify the subject's mucosal healing and response level. No existing single biomarker or multi-biomarker approach has demonstrated a high association and prediction value with mucosal healing and therapeutic endoscopic response in Ulcerative Colitis subjects. The latter is due to the complexity of ulcerative colitis biology and the various immune pathways involved.

In the following description, numerous specific details are set forth to provide a more thorough description of the invention. It will be apparent, however, to one skilled in the pertinent art, that the invention may be practiced without these specific details. In other instances, well known features have not been described in detail so as not to obscure the invention.

Terminology

Throughout the description, the terms individual, subject and patient may refer to a person whose biological data are used to develop and/or use an implementation of the invention. The subject may be normal (or disease-free) or showing any level of symptoms or endoscopic evaluation.

The term biomarker refers to any indicator in any body part (e.g., bodily fluid or tissue) that may be collected and the presence of which measured through any of its manifestations such as protein, peptide, enzymatic activity, mass, concentration, cell count, cell shrinkage/shape, deoxyribonucleic acid (DNA) and/or ribonucleic acid (RNA) genetic level of expression or any aspect of the biochemical or the physiological markers that may be related to one or more health conditions. Moreover, for the purpose of designing health status indices (see below) a biomarker data may be any related data that may be considered for diagnosing or monitor a disease (or the probability of occurrence thereof) such as age, sex, any biometric data, genetic history (e.g., parent's health status or presence of any affection in the family) or any other data that may contribute to the diagnosis, monitoring of a disease and related treatment decision.

The term "test" is used in multiple contexts in the description. In the context of determining the level of biomarkers, a "test" refers to all necessary steps involved in determining the level (e.g., concentration, enzymatic activity etc.) of each biomarker in a biological sample. In the context of a panel of biomarkers, a "test" refers to measurement of each biomarker in the panel. Measurement of biomarkers yields numbers. In the context of data analysis, a "test" is used to refer to the calculation(s) carried out on the numbers, which lead to a determination whether a first data set is significantly different from a second data set.

The term "index" is used throughout the disclosure to refer to a dependent variable that is calculated using two or more data inputs such as the level of two or more biomarkers in the bodily fluid or tissue.

The term "user" may be used to refer to a person, machine or a computer program acting as or on behalf of a person carrying the steps of the invention. The invention may be practiced by a person carrying out the steps of the methods disclosed herein and using the systems disclosed in the invention and/or by implementing the method steps of the invention in a machine that (fully or partially) automatically carry out the measurement of biomarkers and determination of the level of mucosal healing.

In the disclosure, statistical data of a population may be presented as media and inter quartile range (IQR) or quartile (Q). When presented as median IQR, the numbers are shown as a set of a first number, which is the median, followed by two numbers in parentheses. The two number in parentheses are separated by a hyphen or a "to" to indicate a range, and they present the first and third quartile values, respectively, of the population. When presented as quartile (Q), the numbers are shown as a number, which is the quartile.

When measuring biomarkers in a blood sample, whole blood, plasma and/or serum portions may be considered for the measurement. Unless otherwise specifically pointed out, the invention may utilize the serum portion or the plasma portion of a blood sample. The use of either term in this disclosure implies the use of either the plasma portion or the serum portion. It is also understood that when implementing the invention, a first method to measure a first biomarker may require the use of a serum portion, whereas a second method used to measure a second biomarker may require the use of whole blood sample or the plasma portion. The invention considers any combination of a required set of blood samples and/or portions thereof to implement the invention as part of the present disclosure.

General Concept of the Invention

The invention utilizes a multi-immune pathway test, involving the measurement of a plurality of biomarkers that are known to be involved in immunological responses albeit without having any apparent known correlation in relation to IBD.

The invention disclosed herein is a novel and powerful method that may be utilized as a replacement of, or in addition to, endoscopic investigation necessary to assess mucosal healing, for example, as a response to treatment of ulcerative colitis patients. An embodiment of the invention provides a practitioner with an computed index that enables the practitioner to assess the level of mucosal healing. The level of mucosal healing is measured by the Mayo endoscopic subscore (MES) change prior and after treatment. For example a MES 3 (non-healing) change to MES 1 or 0 (healing). The method is carried out by measuring the level of several serological biomarkers and using the measured levels to compute the index. The panel of serological biomarkers is selected to reflect changes in several immunological pathways i.e. Multi-immuno pathway test panel.

An embodiment of the invention may be an apparatus, system, kit or any product implementation that enables a practitioner with ordinary skills in the medical field to carry out the steps of the invention. For example, obtaining blood or a portion thereof may utilize one or more techniques for collecting blood from a patient, and extracting plasma and/or serum for measuring the biomarkers. The blood samples and/or serum and/or plasma may be treated (e.g., to preserve the integrity of the samples) with chemicals and/or refrigeration and/or lyophilization, or any other available method used for blood sample collection to make the samples suitable for testing. The methods and any device involved in collecting blood samples are considered herein as a part of the implementation of the invention.

In addition to laboratory equipments for collecting blood or fecal samples, extracting biomarkers and measuring the biomarkers, embodiments of the invention comprise computation means such as electronic computers, software program product and any product that may be involved in providing a tool for assessing mucosal healing in any patient in accordance with the methods disclosed herein.

FIG. 1 is a flowchart diagram representing steps involved in developing a non-invasive method for assessing mucosal healing in subjects undergoing treatment for ulcerative colitis, in accordance with an embodiment of the invention.

Step 130 represents collecting data from a group of subjects. The group of subjects may be a sample of subjects comprising normal subjects (i.e. healthy) or unaffected by ulcerative colitis, and affected subjects showing any level of severity of symptoms and/or other indicators. Bodily fluids (e.g., Urine and/or stool), tissue or any other body sample may be appropriately collected in order to measure the level of a set of biomarkers, such as C-reactive protein, Neutrophil counts, Cathelicidin (LL-37), Chitinase 3-like 1 (CHI3L1), NGAL-MMP-9 etc.

In addition, the subjects may undergo a plurality of tests, such as endoscopy, histological, radiological tests or any other test designed to establish the level of presence or absence of the target disease(s).

Moreover, other non-disease related data may also be considered. The latter data comprise age, sex, any biometric data, genetic history (e.g., parent's health status or presence of any affection in the family) or any other data that may contribute to the diagnosis of a disease.

The level of each biomarker may be expressed in one or more unit types that characterizes the level of the presence of the biomarker in the body fluid/tissue under consideration. Thus, an enzyme may be characterized by the level of its enzymatic activity, a protein or a peptide, a hormone or any other biomarker may be expressed by a concentration level such as its mass or moles per volume of tissue or bodily fluid.

Step 140 represents the process of defining range values for each biomarker, and involves discretizing the data, which comprises attributing a score number to each previously defined range of a biomarker level. For example, the level of CRP may be represented by two ranges, the first range may be attributed the value zero (0) and the second range may be attributed the value one (1).

Step 150 represents computing an index value for each subject as follows:

$$I = \sum_{i=1}^{i=N} C_i \cdot L_i \tag{1}$$

where the index value "I" for each subject may be the sum of the product of the score level "L" (e.g., computed at step 140) and a coefficient "C" associated with the "$i^{th}$" data input for a number "N" of data inputs (e.g., biomarker level, age, biometric data etc.). The coefficient "C" may be determined empirically as shown below at steps 160 and 170.

Step 160 represents applying one or more methods for segregating subjects using the health status data and the computed index values. For example, the method of segregation may be the Receiver Operating Characteristic (ROC) curve analysis. ROC curve analysis is a well known method in the medical field for determining whether a correlation between the level of a biomarker may serve as an indicator of the presence of a health condition. The latter is possible for example when there is a strong correlation between the amount of a substance in the body (e.g., high cholesterol) and a health condition (e.g., sclerosis of blood vessels).

Using the ROC curve analysis on the index values of all subjects in the group, it is possible to determine whether there is a cutoff value capable of classifying individuals into groups matching their health status. For example, if subjects are responding to a treatment (healers/responders) are labeled as positive and the non-healers/non-responders are labeled as negative, the ROC curve analysis may yield a threshold that classifies the subjects into an above and a below-threshold groups matching the health statuses responders and non-responders to treatment, respectively. There may be false positives and false negatives for each chosen cutoff value in the range of possible values. The rate of success in determining true positive cases is called "Sensitivity", whereas the rate of success in determining true negative cases is called "Specificity". Sensitivity and specificity for a plurality of cutoff values are computed. Sensitivity and Specificity are rates, and thus may be expressed in the range of zero (0) to one (1), or as a percentage from zero (0) to one hundred percent (100%). The results are plotted as Sensitivity values versus one (1) (or 100% depending on the unit of choice) minus the corresponding specificity. The area under the curve (AUC) reveals whether ROC analysis may be a valid classifier of the data: the closer the AUC is to 100%, the better classifier is the ROC analysis. On the contrary, the ROC analysis may not be considered for classification purposes if the AUC is closer to 50%, which is considered close to a random process. In general, the ROC method of analysis may be considered valid, if the AUC is at least 0.8 (i.e. 80% of the total possible area under the curve).

Moreover, each threshold value yields a "Sensitivity" and "Specificity". In populations where ROC analysis appears adequate, the "Sensitivity" curve decreases as the "Specificity" increases. At a particular threshold, the apex, the total of Sensitivity and Specificity is at a maximum. The apex is typically chosen as the threshold of classification if it yields a Sensitivity and Specificity each above 0.85, otherwise a threshold for Specificity and a threshold for Sensitivity may be respectively selected to yield a success rate of at least 0.85.

ROC analysis is one of any existing methods that may be utilized in embodiments of the invention to detect clusters in the data that define the clustering boundaries capable of segregating subjects into groups matching health status categories. For example, k-means clustering, hierarchical clustering, neural networks or any other clustering method may be utilized in one or more embodiments of the invention. Furthermore, an embodiment of the invention may conduct the steps of FIG. 1 using a plurality of methods of clustering the data to achieve the results of the invention. The final clustering method that may be retained in any particular embodiment of the invention may be the one that yields the highest success rate of a predictive model for mucosal healing in patients undergoing treatment for ulcerative colitis.

Analysis of computed index data is further carried out using Cox proportional hazards regression model (also referred as Cox regression), a method that provides estimate of survival probabilities (as an outcome) within a given time interval. For the purpose of the present invention, the Cox regression is carried out using index value in lieu of time intervals and mucosal healing as a the outcome. The latter analysis further reinforces the index, as disclosed in the invention as a robust predictor of mucosal healing.

Step 170 represents computing success scores of the method of segregating of subjects in the test group. If the success level of the segregation into health categories is not satisfactory (e.g., no statistical difference compared to a population drawn from a random process), the parameters for computing the index values are revised and the analysis is repeated at step 140. The process of searching for optimal parameters may be repeated until the result of classification of subjects reaches (or exceeds) an acceptable success rate. Otherwise, if no optimal parameters may be found, the result may indicate that the chosen set of biomarkers is unsuitable for segregating the subjects, based on the index method under consideration, into the proposed health status categories.

The search for optimal parameters may involve changing one or more boundary values for discretizing biomarker values, and/or the weight coefficients associated with each biomarker in computing the index value for each subject. The search method may be manual i.e. an expert practitioner may set the initial parameters and adjust them, through multiple iterations of computation, while considering the outcome of the success rate of classification of subjects into health status categories. Implementations of the invention may also use numerical methods for automatic search to optimize parameters. Such methods comprise brute force search, where a large number of values of parameters and combinations thereof are tested. The numerical methods for determining optimal values may use gradient descent search, random walk search or any other mathematical method for searching for optimal parameters in order to achieve the goal of maximizing the success rate of the classification of subjects into correct corresponding health status categories.

Computer programs for conducting a search, in accordance with an implementation of the invention, require ordinary skills in the art of computer programming. Moreover, existing computer programs may be adapted (through a programming scripting language) to carry out a search process in an implementation of the invention. Any available computer program may be used, including, for example, the following computer programs identified by their respective registered trademark as follows: Mathematica™, Matlab™ Medcalc™.

Step 180 represent the final step of determining the final parameters (or ranges thereof) that may be used in a predicting a specific outcome (e.g., mucosal healing). The optimal parameters include the coefficient associated with each biomarker, the number of ranges and the boundary values that define the ranges for each biomarker. Step 180 also includes determining the index range boundaries that define the categories (level of mucosal healing) as defined by the health status of subjects determined by endoscopy.

Defining range boundaries as discrete values may be carried out during the search for the optimal parameters (as described above). The discrete range boundary values may also be provided computationally (e.g., using multipliers and offsets) subsequent to determining the optimal parameters.

In one embodiment of the invention, the coefficients have been selected so that the index values would range between 0 and 10. The latter is selected for convenience of use by practitioners while using the method of the invention to perform diagnoses. However, the invention allows one to select any range to express the index. The latter may be achieved using any scaling mathematical function, such by using a multiplying and/or an offset number. Any index range that may be obtained by manipulating the numbers disclosed below is considered part of the disclosed invention.

The invention cites (below) specific cut-off values for obtaining the discretized values and other values for segregating responders versus non-responders. Each disclosed value should be interpreted, in the context of the present disclosure, as representing a range of values within which the optimal results can be obtained according to the invention.

The biomarkers according to the invention are: C-reactive protein (CRP), the complex of neutrophil gelatinase-associated lipocalin and matrix metalloproteinase-9 (NGAL-MMP-9), Neutrophils count, LL-37, which is the active anti-microbial peptide of cathelicidin and Chitinase 3-like 1 (CHI3L1). Although each of NGAL-MMP-9, Neutrophils, LL-37, CHI3L1 and CRP provides valuable dataset for Ulcerative Colitis mucosal healing, none of these biomarkers alone is indicative of mucosal healing the level of mucosal healing. In fact, using the Receiver Operating Characteristic (ROC) analysis for each biomarker, the area under the curve of the analysis (also referred as sensitivity) covers less than 50% of the ulcerative colitis patients. Developing multi biomarkers based test sensitive and specific to mucosal healing of ulcerative colitis has proven difficult in practice because of the complexity of ulcerative colitis biology and various immune pathways involved. Adding to the difficulty of developing a specific multi biomarkers based test are reduction in specificity and the technical challenges involved such as neutrophils that can burst in serum. No existing single biomarker or multi-biomarker approach has demonstrated a high association and prediction value with mucosal healing and therapeutic response in Ulcerative Colitis subjects. Additionally, weighting a subject therapeutic windows several weeks after treatment initiation has never been addressed using a multi-biomarker test.

The invention provides a simple index that allows a practitioner administering a treatment to obtain the index, store data, share and compare the data among and between several institutions (e.g., hospitals and/or clinics) and take treatment decisions such as continuing the use of a therapeutic agent or switching to another therapy.

The benefits of implementations of the invention are numerous. In addition, to monitoring the progress of mucosal healing during treatment, enabling physicians to make decisions to switch treatment earlier for UC patients who fail to achieve healing with their first treatment choice, thus reducing the number of flares and hospitalizations that occur when waiting for endoscopic evaluation. The invention also provides a predictor for determining those subjects that will have endoscopic response to treatment versus those that do not or will respond at a lesser level. Additionally, the invention allows for weighing a subject's therapeutic windows prior to regular endoscopy evaluation, which has never been addressed using a multi-biomarker test.

C-Reactive Protein (CRP)

CRP is a pentameric, acute-phase protein made by hepatocytes (Tillett et al. J Exp Med. 1930 Sep. 30; 52(4):561-71) The half-life of CRP is 19 hours, which allows for rapid rising and falling of levels with onset of and resolution of inflammatory states, respectively. Healthy individuals have low levels of CRP in circulation, usually less than 1 mg/L, but levels can rise 100-fold in periods of acute inflammation (Fengming et al. Dis Markers. 2014). In IBD, CRP has been significantly associated with other biomarkers of inflammation including ESR, thrombocytosis, anemia, and hypoalbuminemia (Solem et al. Inflamm Bowel Dis. 2005 August; 11(8):707-12). CRP is often used to monitor for occult internal inflammation when patients are clinically asymptomatic. In contrast with CD patients, in whom CRP is an accurate marker, CRP is normal in more than 50% of ulcerative colitis patients (Magali et al. Inflamm Bowel Dis 2014; 20:1198-1207).

Fecal Calprotectin

First described in 1980, calprotectin is a 36 kilodalton inflammatory protein found in the cytosol of human neutrophils, macrophages, and monocytes (Smith et al. World J Gastroenterol 2012; 18: 6782-6789.) Calprotectin comprises up to 60% of neutrophil cystolic proteins. The presence of calprotectin in the feces is directly proportional to neutrophil migration into the gastrointestinal tract during times of inflammation (Vermeire et al. Gut 2006; 55: 426-431). Fecal Calprotectin (FC) is a stable marker, resistant to degradation, that can be detected in stool for more than one week at room temperature (Røseth et al. Scand J Gastroenterol 1992; 27: 793-798.) Takashima et al. (Am J Gastroenterol 2015; 110: 873-880) showed significant correlation of Mayo endoscopic scores with FC (r=0.58; p<0.0001) in 92 patients with UC. In the meta-analysis by Mosli et al. (Am J Gastroenterol 2015; 110: 802-819), FC predicted endoscopic activity with overall higher sensitivity than CRP, as expected. The pooled sensitivity and specificity of FC for endoscopically active IBD was 88% and 73%, respectively. When ulcerative colitis and CD were considered separately, ulcerative colitis exhibited equivalent sensitivity (88% vs 87%, respectively) but superior specificity (73% vs 67%) when compared to CD. An optimal FC cutoff of greater than 50 µg/g was calculated to signify endoscopically active disease.

In ulcerative colitis patients using infliximab where a fast and significant fall in calprotectin concentrations occurred (median at baseline 1,260 µg/g and at week 1,073 µg/g) (De Vos et al. J Crohns Colitis. 2012 June; 6(5):557-62). The decrease in calprotectin at week 2 predicted a remission at week 10. However remission was not complete at week 2 since calprotectin level of 50 mg/kg or a decrease of at least 80% at week 2 predicted an endoscopic remission at week 10 with only a specificity of 67% and sensitivity of 54%.

Neutrophil Gelatinase-Associated Lipocalin and Matrix Metalloproteinase (NGAL-MMP-9) Complex NGAL (Kjeldsen et al. Blood. 1994; 83:799-807) is expressed in response to the activation of Toll-like receptors during infections (Flo et. al. Nature. 2004; 432: 917-921) and it has been shown to inhibit bacterial growth by sequestering iron-laden siderophores. NGAL protein or messenger RNA expression levels are shown to be correlated with parameters of active IBD (Yasil et al. Dig Dis Sci. 2013; 58:2587-2593). MMP-9 is a member of the MMP family. It is a zinc-dependent endopeptidase involved in many developmental processes, including angiogenesis, wound healing, and extracellular matrix degradation. Despite the involvement in many normal physiological processes, MMP-9 has been associated with abnormal disease conditions and is considered a tuner and amplifier of inflammatory reactions. MMP-9 levels have been shown to be elevated in the feces of ulcerative colitis patients and to correlate well with disease activity (Annahazi et al. Inflamm Bowel Dis. 2013; 19:316-320). Recently Sela-Passwell et al. (Nat Med. 2011; 18:143-147) have shown that neutralizing antibodies with tissue inhibitor of MMPs like mechanisms against MMP-2 and MMP-9 can attenuate the development of colitis in IBD mouse models. Studies investigating the decrease of NGAL or MMP-9 after treatment with infliximab were mostly performed in Crohn's disease (CD) patients and not in ulcerative colitis patients. Moreover, the role of NGAL-MMP-9 as a complex has only been investigated in one study, indicating elevated levels of NGAL-MMP-9 in the urine of pediatric IBD patients. Manfredi et al. (Inflamm Bowel Dis. 2008; 14: 1091-1096) showed that urinary NGAL-MMP-9 level was an independent predictor of pediatric IBD. Magali et al showed that serum NGAL-MMP-9 complex levels were increased in patients with active ulcerative colitis compared with HC. NGAL-MMP-9 complex levels significantly decreased after treatment with infliximab and correlated well with mucosal healing. These finding of NGAL-MMP-9 complex were complemented CRP in predicting disease activity and mucosal healing.

Neutrophils

Polymorphonuclear leukocytes (PMN), also called neutrophils, are the most abundant leukocyte population in the blood, comprising 50-60% of the circulating leukocytes (25×109 cells) (Sadik et al., Trends Immunol. 2011 32, 452-460). PMN are critical components of the innate immune response that are essential in protecting the host from microbial pathogens, while also minimizing deleterious effects mediated by dying or injured cells. PMN are elegantly adapted to perform a variety of antimicrobial functionssuch as degranulation and phagocytosis (below Figure—BM Fournier and CA Parkos MucosalImmunology 5 (4) July 2012).

Neutrophils contain a potent antimicrobial arsenal. The nicotinamide adenine dinucleotide phosphate (NADPH) oxidase produces reactive oxygen species (ROS), e.g., hydrogen peroxide ($H_2O_2$), hypochlorite ion ($OCl^-$), and superoxide anion ($O_2^-$) in the phagolysosome during phagocytosis. Various intracellular granules (azurophil or primary, specific or secondary, gelatinase or tertiary, and secretory granules) containing potent antimicrobial agents are also released in the phagolysosome or in the extracellular space through degranulation. Finally, neutrophil extracellular traps (NETs) are also produced during polymorphonuclear leukocytes activation.

The primary function of neutrophils in the gut is to kill luminal microbes that translocate across the epithelium and invade the mucosa. A good example of the importance of PMN in clearing invading microbes is the enhanced translocation of bacteria observed in colitic mice that have been depleted of PMN (Kuhl et al. Gastroenterology 2007 133, 1882-1892). However, conditions associated with disruption of epithelial barrier leading to increased translocation of commensal bacteria into the mucosa does not necessarily predispose individuals to pathological intestinal inflammation. Indeed, mice lacking junctional adhesion molecule (JAM)-A, a tight junction-associated protein expressed in IECs, have increased epithelial permeability and enhanced translocation of bacteria across the intestinal mucosa but do not get spontaneous colitis despite having increased levels of PMN in the sub-epithelial space or lamina propria (Laukoetter et al. J. Exp. Med. 2007 204, 3067-3076). Presumably, increased recruitment of PMN to the lamina propria and/or some as yet unknown adaptive immune compensatory mechanisms serve a protective role in this situation. However, such compensatory mechanisms are lost under conditions of pathological intestinal inflammation as in IBD. Indeed, it has been observed that increased intestinal permeability results in a significantly increased numbers of commensal bacteria in the colonic mucosa of IBD patients compared with normal individuals. 30 Furthermore, analysis of granulomas in CD revealed the presence of *Escherichia coli* DNA in 80% of patients, suggesting that mucosal-infiltrated bacteria may have a role in the inflammatory process (Ryan et al. Am. J. Gastroenterol. 2004 99, 1539-1543). Insufficient numbers of functional PMN in the intestine during times of increased bacterial invasion might thus predispose to disease. In support of this, it appears that the number of PMN required to prevent bacterial multiplication in tissues is much higher than in the blood. Furthermore, the tissue surveillance capacity of neutrophils depends on the density of the neutrophils rather than the concentration of bacteria (Li et al. J. Exp. Med. 2004 200, 613-622).

Cathelicidin (LL-37)

Cathelicidins are a family of endogenous antimicrobial peptides which form a part of the innate immunity that protects the host from infection (Eckmann L. Defence molecules in intestinal innate immunity against bacterial infections. Curr Opin Gastroenterol. 2005; 21(2):147-51). Cathelicidin exists in human as LL-37 and in mice as mCRAMP (Gudmundsson GH, Agerberth B, Odeberg J, Bergman T, Olsson B, Salcedo R. The human gene FALL39 and processing of the cathelin precursor to the antibacterial peptide LL-37 in granulocytes. Eur J Biochem. 1996; 238 (2):325-32; Gallo R L, Kim K J, Bernfield M, Kozak C A, Zanetti M, Merluzzi L, et al. Identification of CRAMP, a cathelin-related antimicrobial peptide expressed in the embryonic and adult mouse. J Biol Chem. 1997; 272(20): 13088-93). Cathelicidin is secreted from the apical surface that is facing exterior environment such as intestine (Schauber J, Rieger D, Weiler F, Wehkamp J, Eck M, Fellermann K, et al. Heterogeneous expression of human cathelicidin hCAP18/LL-37 in inflammatory bowel diseases. Eur J Gastroenterol Hepatol. 2006; 18(6):615-21) and salivary gland (Murakami M, Ohtake T, Dorschner R A, Gallo R L. Cathelicidin antimicrobial peptides are expressed in salivary glands and saliva. J Dent Res. 2002; 81(12):845-50) by epithelial cells (Schauber J, Rieger D, Weiler F, Wehkamp J, Eck M, Fellermann K, et al. Heterogeneous expression of human cathelicidin hCAP18/LL-37 in inflammatory bowel diseases. Eur J Gastroenterol Hepatol. 2006; 18(6):615-21) and immune cells such as macrophages (Koon H W, Shih D Q, Chen J, Bakirtzi K, Hing T C, Law I, et al. Cathelicidin signaling via the Toll-like receptor protects against colitis in mice. Gastroenterology. 2011; 141(5):1852-63 e1-3). Tran et al reported that Circulating LL-37 Levels accurately Indicate IBD disease activity. In ulcerative colitis patients, serum LL-37 levels in the low and middle titers (below 54 ng/mL) and CRP levels in the higher tertile (>2 mg/L) reflected moderate and severe clinical disease activity (PMS of 5 or above) with similar accuracy. The area under the curve (AUC) of the receiver operating characteristic (ROC) curves for both CRP and LL-37 were around 0.7, suggesting moderate accuracy. Alternatively, serum LL-37 levels in the high titer (>54 ng/mL) and CRP levels in the lower tertile (<0.5 mg/L) reflected ulcerative colitis remission (PMS of 0-2) with moderate accuracy (AUC=0.65). LL-37 was as accurate as CRP in indicating ulcerative colitis disease activity. In attempting to optimize the accuracy of LL-37 as an IBD biomarker, we found that co-existing low LL-37 levels and high CRP levels indicated moderate and severe ulcerative colitis with a high accuracy (AUC=0.80) better than that of either test alone. On the other hand, a combination of high LL-37 and low CRP levels indicated ulcerative colitis remission with higher accuracy (AUC=0.81) than either test alone (AUC=0.64-0.66).

Chitinase 3-Like 1 (CHI3L1)

Chitinase 3-like 1 (CHI3L1) also called YKL-40 is a glycoprotein exhibiting a strong binding affinity to chitin, an abundant polysaccharide found in the cell walls (bacteria, fungi and others), with no apparent glycohydrolase enzymatic activity. CHI3L1 is expressed in a variety of cells (e.g. macrophages, neutrophils, fibroblasts, vascular smooth muscle cells, endothelial cells, epithelial cells, etc.) and is strongly induced at late stages of human macrophage differentiation. In addition, the dysregulation of CHI3L1 was observed in several human diseases characterized by acute or chronic inflammation and tissue remodeling. Recently, Mizoguchi et al. reported that CHI3L1 is specifically upregulated in the colonic epithelial cells and lamina proprial macrophages in the inflamed mucosa from experimental murine colitis and IBD patients. The overexpression of CHI3L1 also increases the adherent-invasive *Escherichia coli* ability to colonize intestinal epithelium. Aomatsu et al. showed a correlation between fecal CHI3L1 level and endoscopic scores in a pediatrics cohort. Buisson et. al. found correlation between fecal CHI3L1 value and endoscopic scores in adults suffering from IBD and shows the performances of fecal CHI3L1 measurement in detecting endoscopic ulceration in Crohn's disease and endoscopic activity in ulcerative colitis adults.

Embodiments of the invention may be implemented using any available method known in the pertinent art to measure the level of any one the biomarkers involved in the embodiment of the invention.

In the case of protein/peptide-type biomarkers, detection by immunoassay is the most common approach due to the specificity and the sensitivity of the available methods insofar as an antibody is available. Reagents required for immunoassay development are the antibodies, signal-generating labels, and separation matrices. Antibodies are the key reagents on which the success of any immunoassay depends. The antibodies can be either polyclonal or monoclonal. The signal generating labels in immunoassays include radioactive atoms (mostly 125I, 3H, and 14C), enzymes, fluorescent probes, chemiluminescent substances, metals and metal chelates, and liposomes. The matrices used for separation of the immune complexes that formed as a result of immunoanalytical reactions include charcoal, polyethylene glycol, second antibody, microbeads and microwell plates.

Numerous immunoassay methods are available in the prior and employ several combination of an antibody, labeling agent and separation matrix listed above. A detailed description to any of the existing methods is readily accessible to one with ordinary skills in the pertinent art. Any of these methods may be employed in embodiments of the invention to detect one or more biomarkers provided by the invention. It would be apparent to one with ordinary skills in the pertinent art that the present invention may be implemented and practiced in several different embodiments. The implementation itself of any embodiment involves considering the target application (e.g., for developing a particular test kit for testing for mucosal healing), without significantly deviating from the gist of the claimed invention.

In the following, exemplary methods that may be employed to assess CHI3L1, LL-37, NGAL MMP-9 and CRP are briefly described. These are exemplary methods that may be utilized to detect these biomarkers to implement the invention. It is understood that any available method for determining the level of any of these biomarkers is inherently included in this description.

Because of its many advantages, enzyme activity is currently the most commonly employed method for detection of the binding of the antibodies with proteins/peptides. Enzyme activity can be amplified without loosing the specificity of the signal. In numerous immunoassay methods, an immune complex is generally provided combining an enzyme and antibodies, thus, providing both the specificity of the method and the availability of amplification.

CHI3L1. In an embodiments of the invention, an assay to measure the level of CHI3L1 may employ the quantitative sandwich enzyme immunoassay technique. A monoclonal antibody specific for human CHI3L1 has been pre-coated onto a microplate. Standards and samples are pipetted into the wells and any CHI3L1 present is bound by the immobilized antibody. After washing away any unbound substances, an enzyme-linked polyclonal antibody specific for human CHI3L1 is added to the wells. Following a wash to remove any unbound antibody-enzyme reagent, a substrate solution is added to the wells and color develops in proportion to the amount of CHI3L1 bound in the initial step. The color development is stopped and the intensity of the color is measured.

LL-37. In an embodiments of the invention, an assay to measure the level of LL-37 may employ the quantitative sandwich enzyme immunoassay technique. Samples and standards are incubated in coated micro titer wells recognizing human LL-37. Biotinylated tracer antibody will bind to captured human LL-37. Streptavidin-peroxidase conjugate will bind to the biotinylated tracer antibody. Streptavidin-peroxidase conjugate will react with the substrate, tetramethylbenzidine (TMB). The enzyme reaction is stopped by the addition of oxalic acid. The absorbance at 450 nm is measured with a spectrophotometer. A standard curve is obtained by plotting the absorbance (linear) versus the corresponding concentrations of the human LL-37 standards (log). The human LL-37 concentration of samples, which are run concurrently with the standards, can be determined from the standard curve.

NGAL-MMP-9. In an embodiments of the invention, an assay to measure the level of NGAL-MMP-9 may employ the quantitative sandwich enzyme immunoassay technique. A monoclonal antibody specific for human MMP-9 has been pre-coated onto a microplate. Standards and samples are pipetted into the wells and any complexed NGAL-MMP-9 present is bound by the immobilized antibody. After washing away any unbound substances, an enzyme-linked monoclonal antibody specific for human NGAL is added to the wells. Following a wash to remove any unbound antibody-enzyme reagent, a substrate solution is added to the wells and color develops in proportion to the amount of complexed NGAL-MMP-9 bound in the initial step. The color development is stopped and the intensity of the color is measured.

CRP. In an embodiments of the invention, an assay to measure the level of CRP may employ the quantitative sandwich enzyme immunoassay technique. A monoclonal antibody specific for CRP has been pre-coated onto a microplate. Standards and samples are pipetted into the wells and any CRP present is bound by the immobilized antibody. After washing away any unbound substances, an enzyme-linked monoclonal antibody specific for CRP is added to the wells. Following a wash to remove any unbound antibody-enzyme reagent, a substrate solution is added to the wells and color develops in proportion to the amount of CRP bound in the initial step. The color development is stopped and the intensity of the color is measured.

Neutrophil Count. An embodiments of the invention utilizes cell counting techniques. Each cell suspended in a conductive liquid (diluent) acts as an insulator. As each cell goes through an aperture, it momentarily increases the resistance of the electrical path between submerged electrodes that are placed on either side of the aperture. This causes a measurable electronic pulse. For counting, the vacuum used to pull the diluted suspension of cells through the aperture must be at a regulated volume. The number of pulses correlates to the number of particles. The height of the electrical pulse is proportional to the cell volume. The method accurately counts white blood cells and erythrocytes.

White blood cells (WBC) Differential Analysis. The white blood cell lytic reagent destroys erythrocytes without significantly affecting leukocytes. The reagent has a preservative which provides a clear separation of the different white blood cell populations including neutrophils. As the sample, prepared for differential analysis, streams through the flow cell these three measurements occur simultaneously on each individual white cell to classify it by cell type:

Low-frequency current measures volume.

High-frequency current senses cellular internal content through measuring changes in conductivity.

Light from the laser bouncing off the individual WBC cells characterizes cellular surface, shape, and reflectivity.

The neutrophil count is calculated by multiplying the white blood cell count by the percentage of neutrophils present.

Detailed Study to Determine Ulcerative Colitis Response Index (UCRI)

A detailed study has been carried out to further affirm the teachings of the invention by following a group of patients who have been treated with Anti-TNF($\alpha$) (Infliximab), who have undergone endoscopy monitoring to assess mucosal healing and from whom blood samples were taken to measure the level of the biomarkers disclosed in the invention. It should be understood that the invention may be practiced in several variations, such as using measurement of biomarkers in other body samples including, whole blood, serum plasma or tissue samples. Embodiments of the invention may be practiced using Anti-TNF($\alpha$) agents other than Infliximab, such as adalimumab, golimumab or their biosimilars such as infliximab-dyyb, infliximab-adba, adalimumab-adbm, adalimumab-atto or a different treatment altogether such as vedolizumab, etrolizumab, ozanimod, tofacitinib. The invention as practiced provides a predictor of the status of mucosal healing regardless of the means of administering treatment for ulcerative colitis.

In accordance with the teachings of the invention, to generate a multi-immune pathway biomarkers panel as a surrogate marker for mucosal healing in ulcerative colitis, serum samples were collected, before and after first treatment with infliximab (IFX) an Anti-TNF($\alpha$) therapeutic, from 145 ulcerative colitis patients. Forty one percent (41%) of the latter patients were female. The median age was 41.3 years, with an inter quartile range (IQR) of 30.8 to 51.9 years of age at the time of follow-up (FU) endoscopy. Serum samples were also collected from 75 controls, 56% of which were female. The median age was 33.6 years with an IQR of 29.2 to 51.8 years. Mucosal Healing (MH) was defined as a Mayo endoscopic subscore (MES) of 0 or 1 (also referred herein as mayo 0-1) at follow-up endoscopy and considered as response to treatment. Table 2 summarizes patient characteristics of Ulcerative Colitis patients from whom serum samples were taken in the development of a multi-immune pathway biomarkers panel as a surrogate marker for mucosal healing.

invention may require, embodiments of the invention may involve developing computer program code to implement the statistical analysis and computation in accordance with the methods taught herein.

Median (IQR) time to serum sampling after start of infliximab was 8.2 (6.0-14.0) weeks. At followup endoscopy, 83 patients were classified as responders or healers with inactive endoscopic disease (MES 0-1 which is also referred as mayo 0-1) and 62 patients as non-responders or non-healers with active endoscopic disease (MES 2-3, which is also referred as mayo 2-3).

Figure 2:
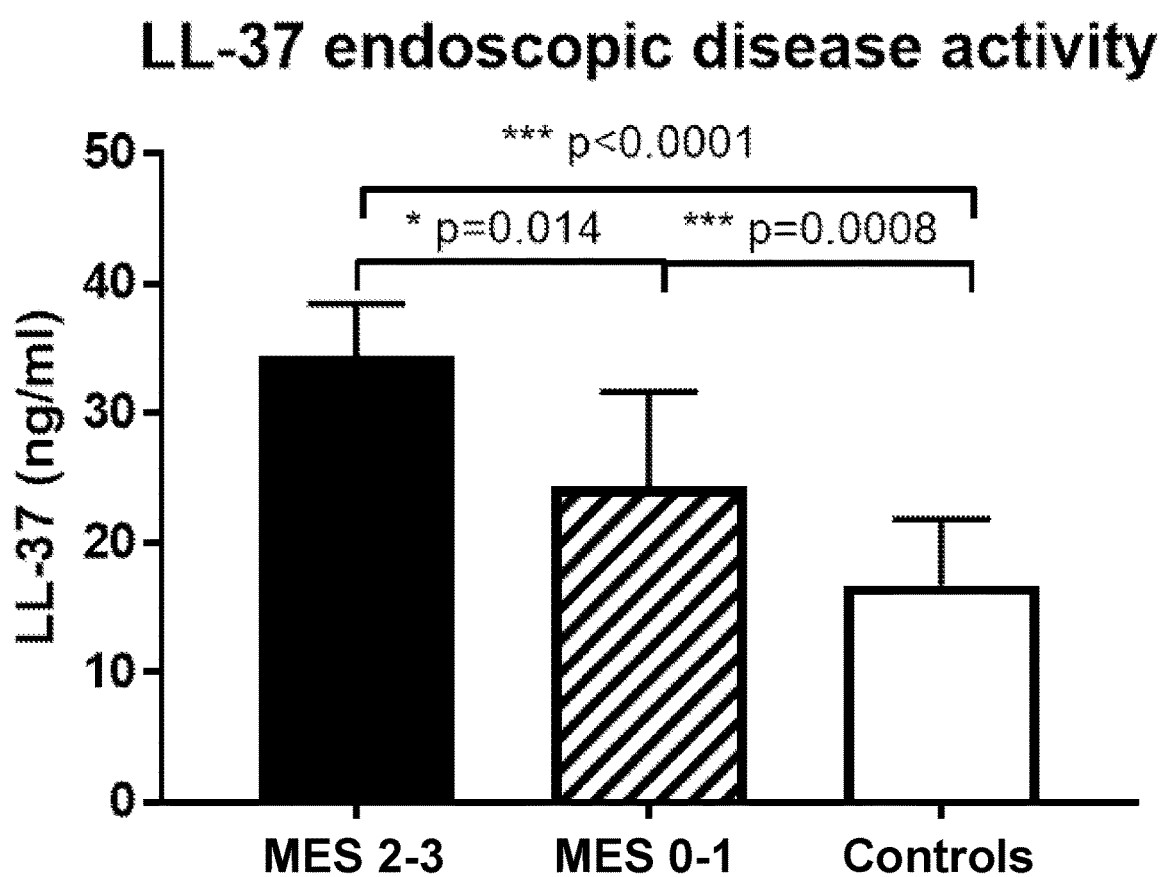
FIG. 2 is a graphical representation of the measurements of human Cathelicidin, LL-37, in a study involving patients showing active endoscopic disease and patients showing inactive endoscopic disease while both were undergoing treatment with infliximab, and involving control subjects, in accordance with an embodiment of the invention.

FIG. 2 is a graphical representation of the measurements of human Cathelicidin, LL-37, in a study involving patients showing active endoscopic disease and patients showing inactive endoscopic disease while both were undergoing treatment with infliximab, and involving control subjects, in accordance with an embodiment of the invention. LL-37 was measured in serum from ulcerative colitis patients with active endoscopic disease (mayo 2-3) i.e. non-responders/non-healers, in serum from patients with inactive endoscopic disease (mayo 0-1) i.e. responders/healers, after treatment with infliximab, and from control individuals (controls).

Median IQR of LL-37 levels were significantly higher in non-healers compared to healers and controls, 37.3 ng/ml (24.0-53.8) ng/ml for healers versus 24.3 (16.1-41.4) ng/ml for non-healers and versus 16.7 (10.2-27.1) ng/ml for controls. The "p" values were 0.002 and p<0.001, respectively.

TABLE 2

| Characteristics at start of IFX | Responders (n = 83) | Non-Responders (n = 62) | P value |
|---|---|---|---|
| Male/Female (%) | 45/38 (54/46) | 41/21 (66/34) | $0.173^a$ |
| Median age (year) (IQR) | 40.3 (28.7-50.1) | 43.4 (33-52.9) | $0.270^b$ |
| Media disease duration (IQR) | 5.9 (2.2-12.5) | 6.7 (1.7-12.1) | $0.977^b$ |
| Disease extent (%) | | | $0.442^c$ |
| E1 (proctitis) | 2 (3) | 0 (0) | |
| E2 (left-sided colitis) | 31 (37) | 22 (35) | |
| E3 (pancolitis) | 50 (60) | 40 (65) | |
| Active smoking (%) | 9 (11) | 8 (13) | $0.796^a$ |
| CRP (mg/l) | 5.7 (1.5-17.0) | 5.5 (3.0-24.5) | $0.236^b$ |
| CRP < 5 mg/l (%) | 38 (46) | 28 (45) | $>0.999^a$ |
| Concomitant treatment (%) | | | |
| 5-ASA | 57 (69) | 57 (91) | $<0.001^a$ |
| Corticosteroids | 30 (36) | 25 (40) | $0.730^a$ |
| Immunomodulators (AZA or MTX) | 47 (57) | 17 (27) | $<0.001^a$ |

$^a$Fisher's exact test,
$^b$Mann-Whitney U test,
$^c$Chi-Squared test

Statistical tests included a Kruskal-Wallis one way analysis of variance on ranks with post-hoc Dunn's multiple comparison procedure or a Mann-Whitney rank sum test used to compare continuous data. Categorical data were compared using a Fisher Exact Test. A receiver operating characteristic (ROC) curve analysis was used to determine the area under the curve (AUC) and select the optimum cut-off value that maximized the Youden's J statistic (sensitivity+specificity-1) for sensitivity and specificity reporting. Significance was set at a p<0.05.

Figure 3:
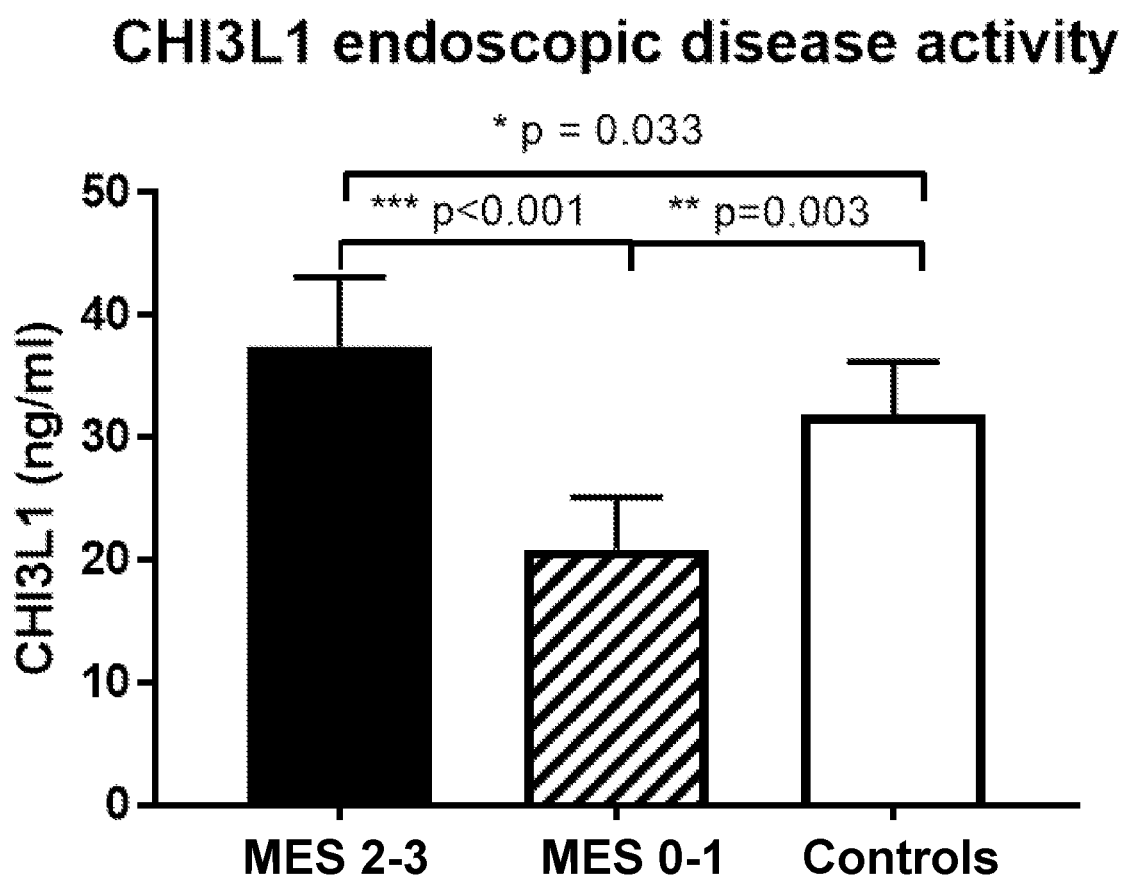
FIG. 3 is a graphical representation of the measurements of Chitinase 3-like 1 (CHI3L1) in a study of patients showing active endoscopic disease and patients showing inactive endoscopic disease while both were undergoing treatment with infliximab and involving control subjects, in accordance with an embodiment of the invention.

The analysis results shown herein were carried out using available computer software, MedCalc software. MedCalc Statistical Software version 16.8.4 (MedCalc Software bvba, Ostend, Belgium; https://www.medcalc.org; 2016). However, embodiments of the invention may utilize any available software. In addition, and an implementation of the FIG. 3 is a graphical representation of the measurements of human Chitinase 3-like 1 (CHI3L1) in a study of patients showing active endoscopic disease and patients showing inactive endoscopic disease while both were undergoing treatment with infliximab and involving control subjects, in accordance with an embodiment of the invention. CHI3L1 was measured in serum from ulcerative colitis patients with active endoscopic disease (mayo 2-3) and inactive endoscopic disease (mayo 0-1) after treatment with infliximab; as well as from control individuals.

Median IQR of CHI3L1 levels were significantly higher in non-healers compared to healers and were comparable to controls 30.0 (22.7-53.9) ng/ml in healers versus 20.9 (14.3-34.4) ng/ml in non-healers and versus 31.9 (19.6-48.6) ng/ml in controls; with values p<0.001 and p=0.424, respectively.

Figure 4:
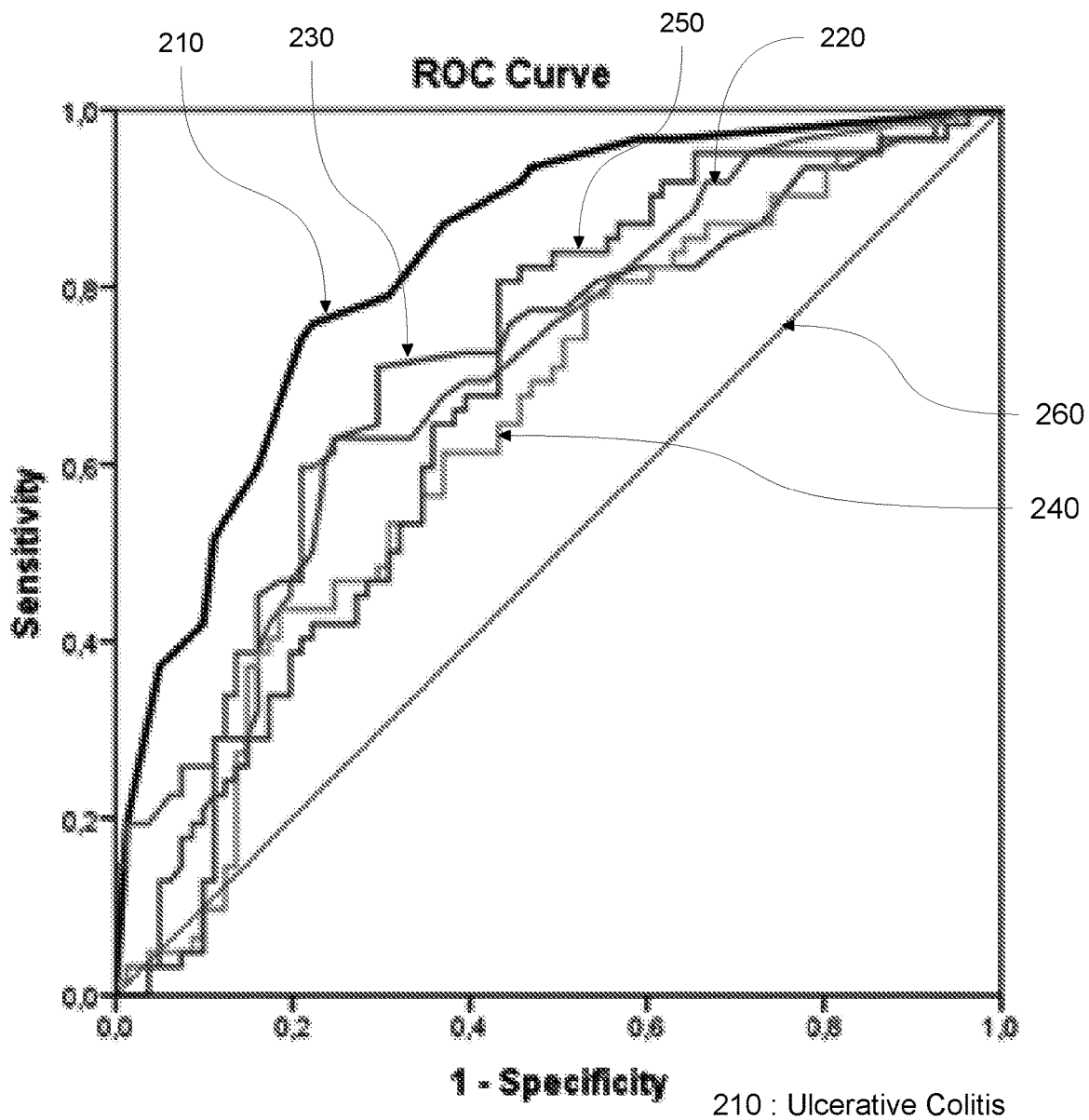
FIG. 4 is a graphical representation of the Receiver Operating Characteristic (ROC) analysis of the measurement data of CRP, Neutrophils, LL-37, CHI3L1 each taken individually and a newly invented ulcerative colitis response index (UCRI), in accordance with an embodiment of the invention.

FIG. 4 is a graphical representation of the Receiver Operating Characteristic (ROC) analysis of the measurement data of CRP, Neutrophils, LL-37, CHI3L1 each taken individually and a newly invented ulcerative colitis response index (UCRI), in accordance with an embodiment of the invention. The measured data of each biomarker was used to generate a binary variable using a threshold value for each biomarker. The binary variables were entered in a logistic regression model. The result is a unit-less index that ranges in value between 0 to 9.8, which is referred herein as the ulcerative colitis response index (UCRI). Line 210 delineates the ROC curves for UCRI, while lines 220, 230, 240 and 250 delineate ROC curves for biomarkers CRP, Neutrophils, LL-37, CHI3L1, respectively. Line 260 delineates a reference baseline i.e. random ROC curve.

Table 3 summarizes the statistical data analysis represented in FIG. 3.

TABLE 3

| Biomarker/UCRI | AUC | Cut-off |
| --- | --- | --- |
| UCRI | 83% | CRP: 2.8 ng/ml |
|  |  | Neutrophils: 3.5 × 1000/ml |
|  |  | LL-37: 46 ng/ml |
|  |  | CHI3L1: 22 ng/ml |
| CRP | 72% | 2.8 ng/ml |
| Neutrophils | 70% | 3.5 × 1000/ml |
| LL-37 | 65% | 46 ng/ml |
| CHI3L1 | 68% | 22 ng/ml |

Table 4 (below) shows the cut-off values and discretization scheme used to generate the discrete values.

TABLE 4

| CRP ng/ml | Neutrophils × 1000/ml | LL-37 ng/ml | CHI3L1 ng/ml | Assigned |
| --- | --- | --- | --- | --- |
| <=2.8 | <=3.5 | <=46 | <=22 | 0 |
| >2.8 | >3.5 | >46 | >22 | 1 |

Single cutoff was used for each parameter and binary variables were entered in a logistic regression model that yield very significant multi-immune Pathway model (MIPM) ($P<0.0001$). MIPM was built to generate an index—Ulcerative Colitis Response Index (UCRI)—to identify healers and non-healers.

Table 5 (below) summarizes the statistical analysis data.

TABLE 5

| Variable | Coefficient | SE | Odds Ratio | 95% CI |
| --- | --- | --- | --- | --- |
| LL-37 | a = 0.9 +/− 0.2 | 0.47 | 2.5 | 1.0 to 6.4 |
| Neutrophils | b = 1.6 + 0.1 to 0.4 | 0.42 | 4.9 | 2.1 to 11.2 |
| CRP | c = 1.2 + 0.1 | 0.42 | 3.23 | 1.4 to 7.5 |
| CHI3L1 | d = 1.1 + 0.1 | 0.46 | 3.1 | 1.2 to 7.6 |

Thus, the ulcerative colitis response index according to one embodiment of the invention may be expressed as formula (2), where UCRI stands for the computed index and dLL-37, dNeutrophils, dCRP and dCHI3L1 stand for discretized values of measured quantities of LL-37, Neutrophils, CRP and CHI3L1, respectively, and where coefficients a, b, c and d are as shown in the second column of Table 5. "n" is a scaling factor and has the value two (2) in this instance to provide a range of 0 to 10.

$$UCRI = ((a \times dLL\text{-}37) + (b \times dNeutrophils) + (c \times dCRP) + (d \times dCHI3L1)) \times n \quad (2)$$

Non-parametric tests were performed and p-values <0.05 were considered significant. The Area Under the Curve (AUC) of UCRI was 0.83 and Q1 (0.0-2.6) was able to discriminate healing with 54% sensitivity, 92% specificity, 60% Negative Prediction Value (NPV) and 90% Positive Prediction Value (PPV), whereas Q4 (7.2-9.8) was able to discriminate non-healing with 37% sensitivity, 95% specificity, 67% NPV and 85% PPV.

As stated above, the cut-off values described in Table 4 are each representative of a range of values that yield the diagnoses results sought by the invention. The range represented by each value as tested had a tolerance in general close to the value +/−10%.

Moreover, as stated above, the invention may be practiced using other methods to measure one or more biomarkers. Each value obtained by any specific method will have a variance that depends on the accuracy of that method. It is therefore assumed that when the invention is practiced with a method different from any described above, that the practitioner makes an appropriate adjustment of the values to use in the index. The ranges of values, obtained from those adjustments, are also considered as part of the present disclosure. Biomarker ranges are selected based on the level of accuracy that the invention seeks to reach. It is evident that when a method has been modified to fit any particular need while implementing the invention, that the ranges and cutoffs may be modified accordingly. The disclosure teaches every aspect of the invention that would allow one with ordinary skills in the pertinent art to easily adapt the invention to a particular application (e.g., test kit).

Figure 5:
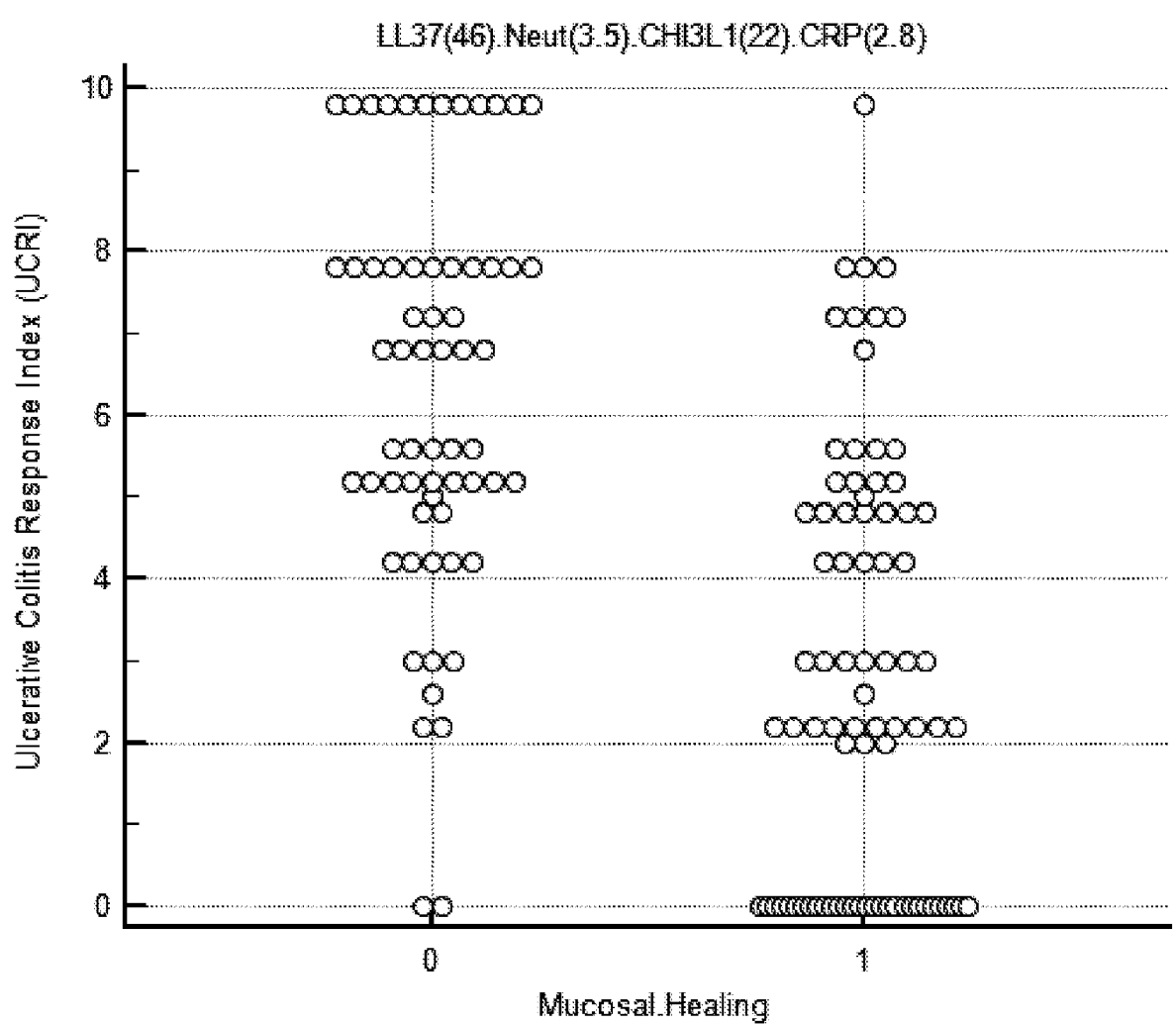
FIG. 5 is a scatter plot of computed ulcerative colitis response index values in relation to the mucosal healing as determined by other (endoscopic) means in accordance with a study conducted according to the invention.

FIG. 5 is a scatter plot of computed ulcerative colitis response index values in relation to the mucosal healing as determined by other (endoscopic) means in accordance with a study conducted according to the invention. UCRI is shown as a unit-less index that takes values between 0 and 9.8. Each data point (open circle) represents an individual patient. Each patient is graphically represented as non-responder (i.e. health status "0") or a responder (i.e. health status "1"). FIG. 5 graphically reveals that non-responders ("0") tend to aggregate at higher levels of UCRI values, while responders (i.e. "1") tend to aggregate toward low values of UCRI. Thus, a subject having value "0" is most likely a responder (healer) and a subject having value "9.8" is most likely a non-responder (non-healer).

In order to further determine whether UCRI is with a predictor of mucosal healing, data were analyzed employing Cox Proportion Hazards regression for survival time model. The variables in the model typically referred as "Time" and "Survival" in this model are substituted for the purpose of the study with UCRI and mucosal healing values, respectively. Table 6 summarizes the results of the analysis.

TABLE 6

| | Baseline | At Mean of Covariates | |
| --- | --- | --- | --- |
| UCRI | Cumulative Hazard | Cumulative Hazard | Survival |
| 0 | 0.03 | 0.01 | 0.99 |
| 2.2 | 0.08 | 0.03 | 0.97 |
| 2.6 | 0.10 | 0.04 | 0.96 |
| 3 | 0.18 | 0.07 | 0.93 |
| 4.2 | 0.32 | 0.12 | 0.87 |
| 4.8 | 0.39 | 0.15 | 0.86 |
| 5 | 0.43 | 0.16 | 0.85 |
| 5.2 | 0.78 | 0.29 | 0.75 |
| 5.6 | 1.04 | 0.39 | 0.68 |
| 6.8 | 1.43 | 0.53 | 0.57 |

TABLE 6-continued

| | Baseline | At Mean of Covariates | |
|---|---|---|---|
| UCRI | Cumulative Hazard | Cumulative Hazard | Survival |
| 7.2 | 1.67 | 0.62 | 0.57 |
| 7.8 | 2.72 | 1.01 | 0.36 |
| 9.8 | 5.5 | 2.05 | 0.13 |

Figure 6:
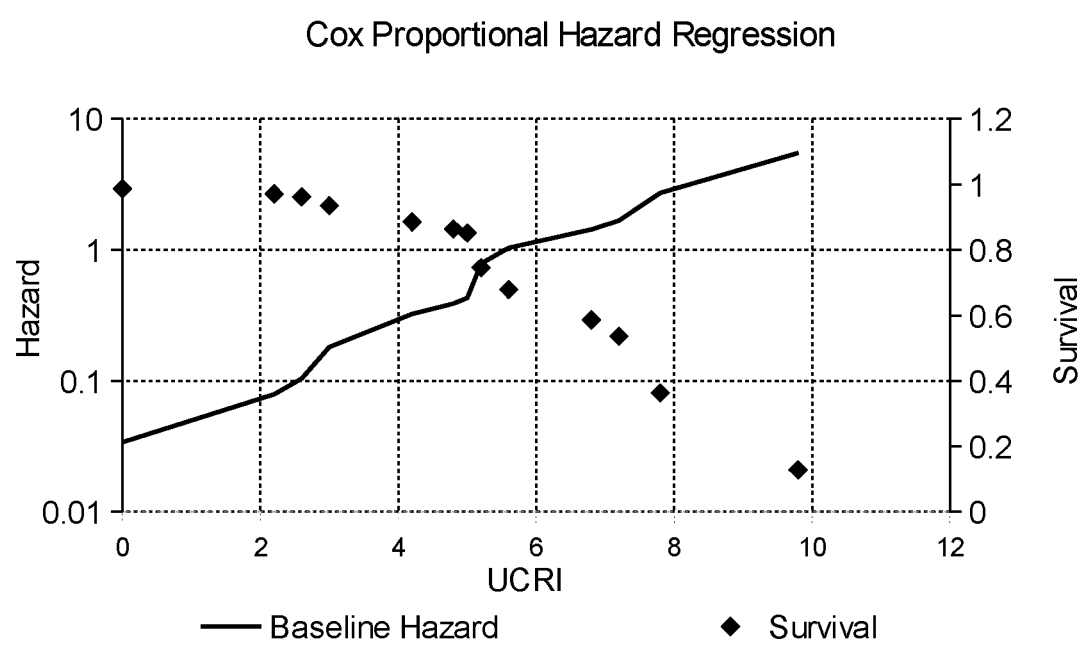
FIG. 6 is a graphical representation of the survival ratio and the baseline hazard in relation to the Ulcerative Colitis Response Index in accordance with an embodiment of the invention.

FIG. 6 is a graphical representation of the survival ratio and the baseline hazard in relation to the Ulcerative Colitis Response Index in accordance with an embodiment of the invention. As UCRI increases the hazard ratio increases to be a non-responder (non-healer). Hazard ratio (HR) ranges from 0.03 to 5.5. At UCRI of 5.6 HR crosses 1.0.

The above result shows that UCRI is indicative of mucosal healing as early as 3 weeks after IFX initiation (Hazard ratio, 95% CI, 4.1 (2.6-6.5)). The later finding of the invention is very valuable to a practitioner in determining early endoscopic response to treatment, since it enables a change in therapy prior to endoscopic analysis.

The study further questioned whether UCRI may be an indicator of mucosal healing at any given specific time (or time range) during the treatment. Data were collected at several intervals from the beginning of the treatment for a period ranging from one to twenty four weeks (1-24 weeks). At each interval, a cohort of patients undergoes endoscopy and provide serum samples. Serum samples are analyzed in the accordance with the invention. Patients data were analyzed using endoscopic response rates according to time of sampling after infliximab based on UCRI (including CRP, CHI3L1, neutrophil count and LL-37). A UCRI threshold is determined in accordance with the teaching of the invention (as described above). Patients are then segregated on the basis of their UCRI as being in the group of responders (healers) (below the UCRI threshold) or in the group of non-responders (non-healers) (above the UCRI threshold). Within each group, a percentage of actual responders (as determined by endoscopy) is calculated.

Figure 7:
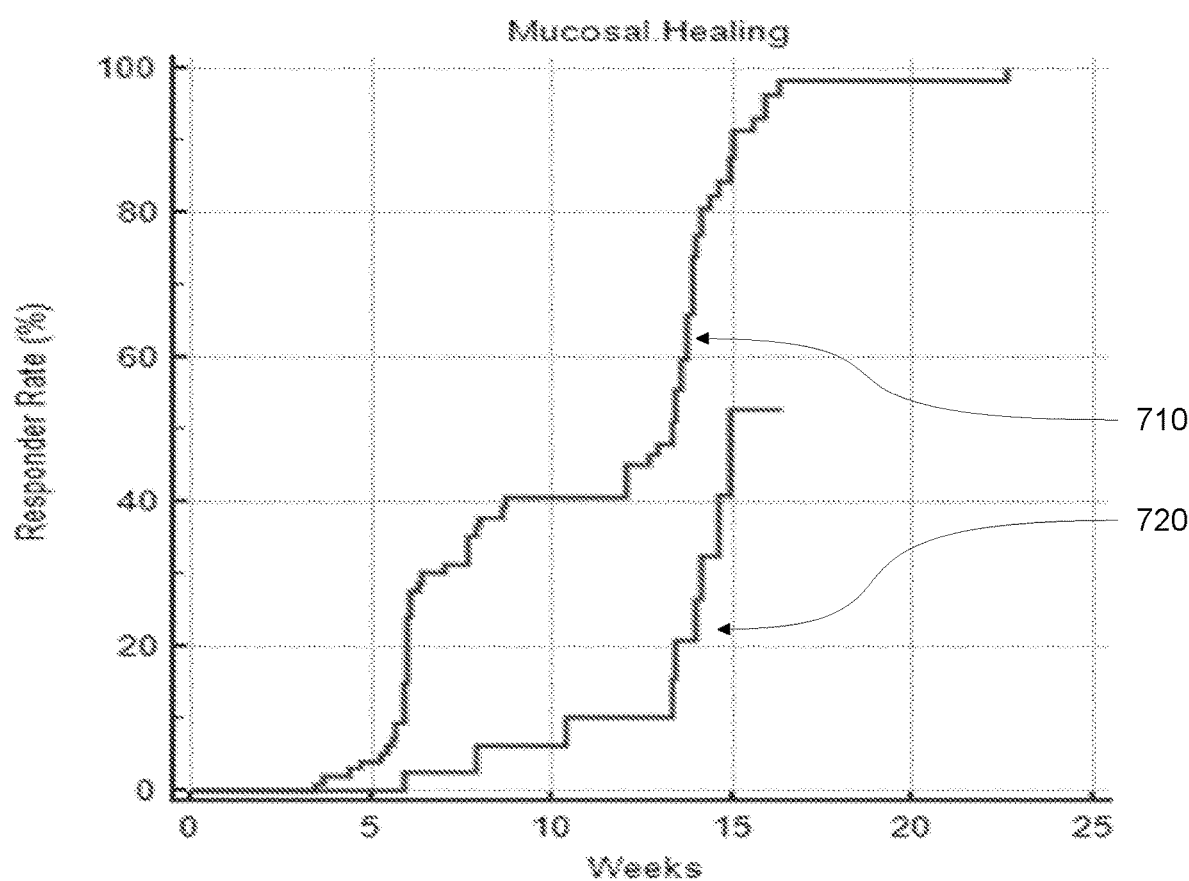
FIG. 7 is a graphical representation of responders and non-responders rates in relation to time interval between the beginning of treatment and endoscopy.

FIG. 7 is a graphical representation of responders and non-responders rates in relation to time interval between the beginning of treatment and endoscopy. The responders group 710 showed an improved hazard ratio compared to the non-responders patients 720. The analysis, and FIG. 7 illustration, shows that the responders group consistently has a higher mucosal healing rate at any given time during the treatment as compared with the non-responders group.

The study further questioned whether UCRI could be beneficial in assessing the mucosal healing at time intervals shorter than twenty four weeks. The latter would be extremely beneficial to practitioners administering the treatment to evaluate whether a patient is properly responding to a drug, which would help in adapting the treatment. A subset of patients was analyzed for those measurements conducted within ten weeks from the beginning of the treatment.

Figure 8:
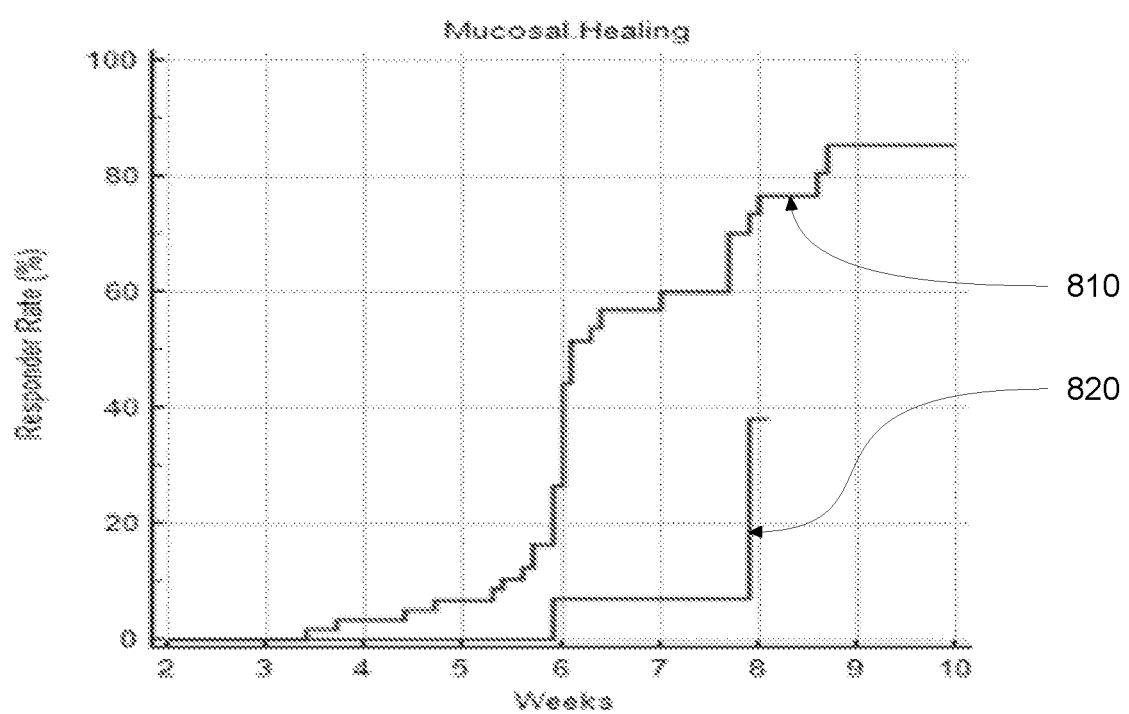
FIG. 8 is a graphical representation of responders and non-responders rates in relation to time interval between the beginning of treatment and ten (10) weeks through treatment.

FIG. 8 is a graphical representation of responders and non-responders rates in relation to time interval between the beginning of treatment and ten (10) weeks through treatment. As in FIG. 7, the responders 810 showed an improved hazard ratio compared to the non-responders patients 820. The responders group consistently has a higher mucosal healing rate at any given time during the treatment as compared with the non-responders group. More importantly for this analysis, by week ten (10), the rate is above eighty percent (80%) within this group.

Thus, the results illustrated in FIGS. 7 and 8 demonstrate that UCRI is a predictor of mucosal healing as a response to treatment with infliximab throughout duration of the treatment period. UCRI thus allows a practitioner to assess the level of mucosal healing throughout the treatment period.

Predictive Capability of UCRI of the Mayo Endoscopic Subcores

UCRI score of the invention has been measure and analyzed in a study that related the UCRI with the mucosal changes as determined by repeated endoscopic tests, and reported as a the Mayo endoscopic subscore (MES). The latter analysis is to determine whether UCRI may be used as a predictor for MES. MES have been determined in subjects under study while serum samples were analyzed in accordance with the teachings of the invention.

Figure 9:
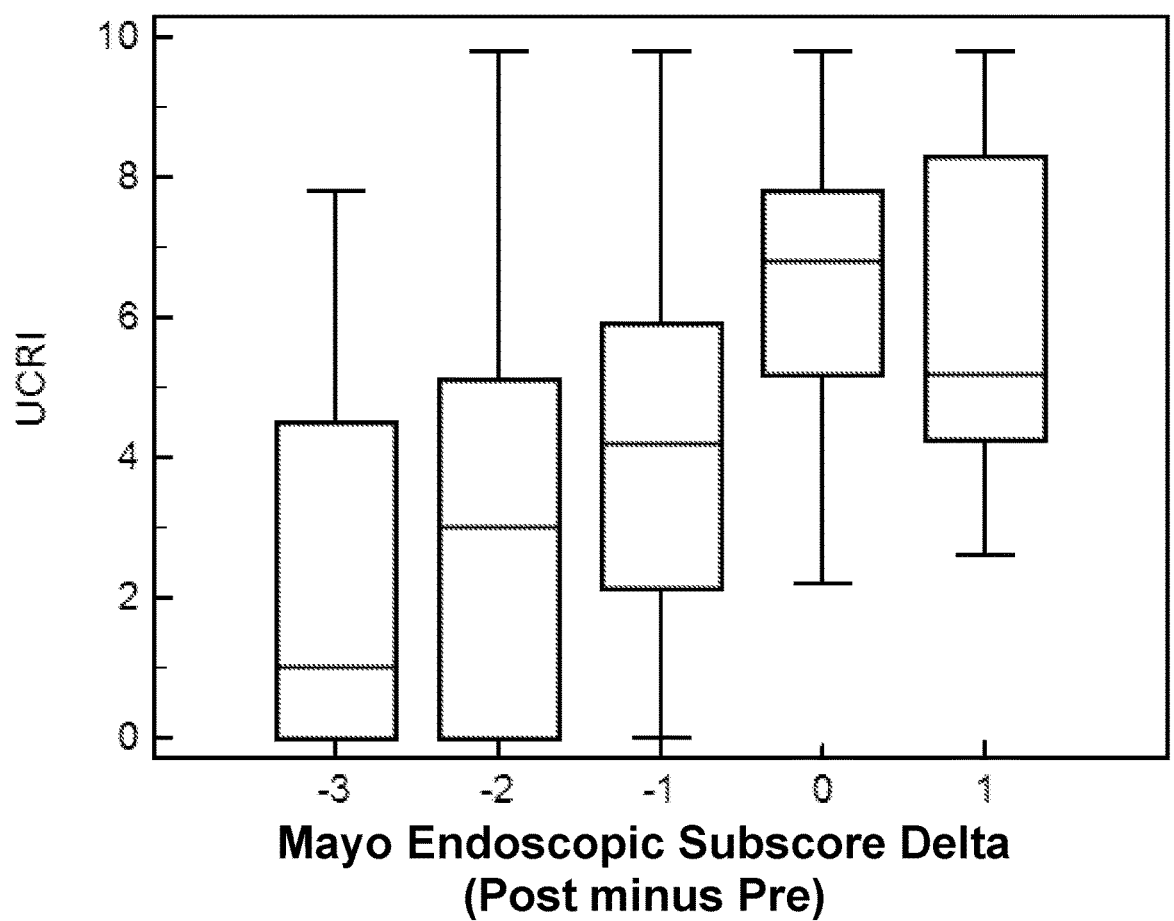
FIG. 9 is a graphical representation of the Ulcerative colitis response index in relation to the evolution of mucosal healing as assessed by the May score.
Figure 10:
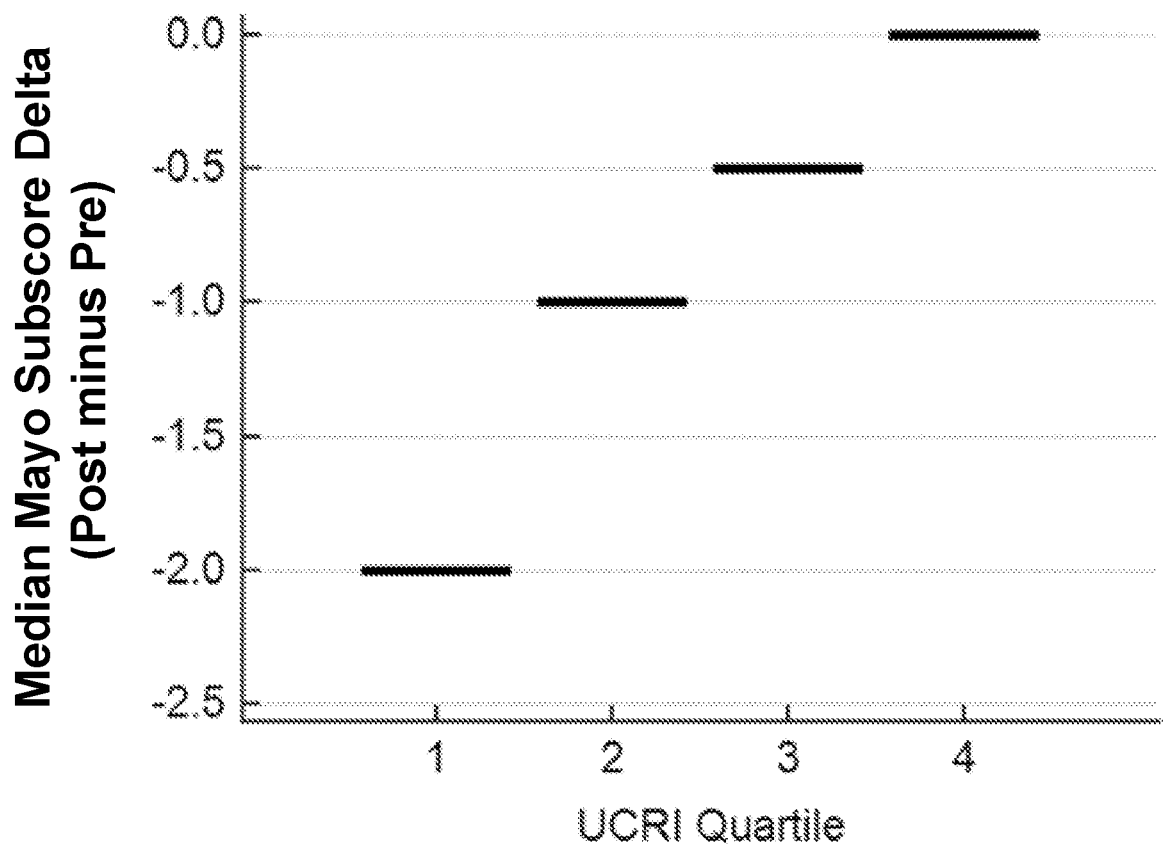
FIG. 10 is a graphical representation of the evolution of mucosal healing as assessed by the Mayo endoscopic subscore in relation with to the Ulcerative colitis response index ranges represented as quartiles.
Figure 11:
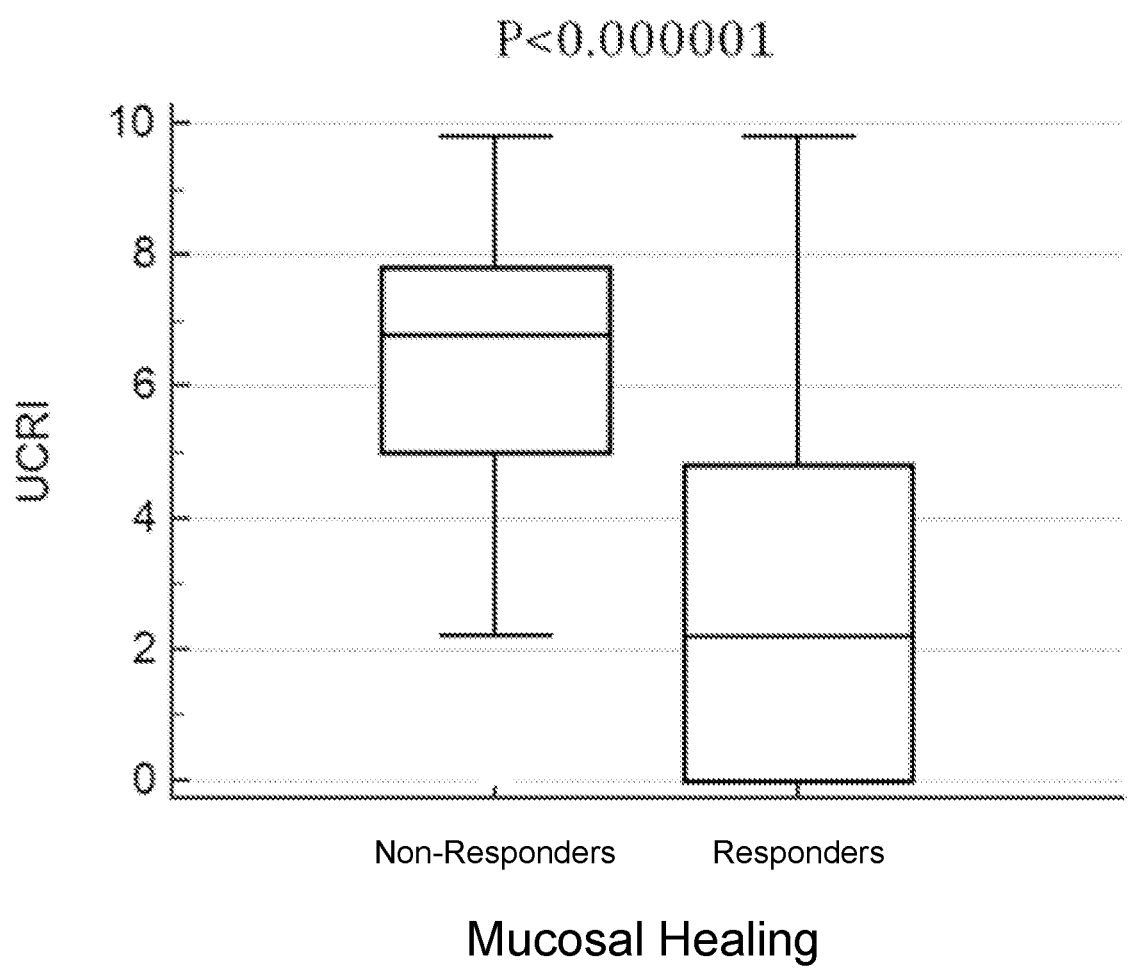
FIG. 11 is a graphical representation illustrating a statistical correlation between the Ulcerative colitis response index values and the mucosal healing assessed in groups of responders and non-responders.

The results, as illustrated in FIGS. 9, 10 and 11, show that the UCRI score tightly reflects the net change in endoscopic score change or delta. The results show that a high UCRI score indicates that patients are non-responders and tend to have no (0) change or even a worse endoscopic MES (+1). On the contrary, low UCRI scores are indicative that patients are responders and have a net negative change in MES (e.g., a 3 becoming a 2).

FIG. 9 is a graphical representation of the Ulcerative colitis response index in relation to the evolution of mucosal healing as assessed by the MES. FIG. 9 shows that when the MES delta is negative, the UCRI is low (e.g., close to "0"), and when MES is zero or positive i.e., no mucosal improvement has been observed, UCRI is high (e.g. in the upper quartile on the UCRI values).

FIG. 10 is a graphical representation of the evolution of mucosal healing as assessed by the Mayo endoscopic subscore in relation with to the Ulcerative colitis response index ranges represented as quartiles. FIG. 10 shows that a value in the upper quartile of the UCRI range is indicative of a MES that has not changed (i.e., non-responders to treatment).

FIG. 11 is a graphical representation illustrating a statistical correlation between the Ulcerative colitis response index values and the mucosal healing assessed in groups of responders and non-responders. The group of non-responders has a significantly higher value of UCRI than a the group of responder.

According to the invention, a patient that shows a UCRI score within the first and second quartiles of the UCRI range should be considered a responder. A patient having a UCRI score in the highest quartile should be considered as a non-responder, whereas a patient having a UCRI score in the third quartile should be monitored and tested subsequently.

Assessing the Propensity to Respond to Treatment Using Biomarkers

The study further questioned whether the biomarkers of the panel of the invention, or a subset thereof, could be used to assess the propensity to respond to treatment with infliximab. To the latter end, serum samples were taken prior to administering the treatment and following up with endoscopic evaluation of patients.

The use of biomarkers LL-37 and neutrophils data combined in a novel method according to the invention are shown herein to predict which patients would be responsive and healed by the treatment and which would not. In a preliminary analysis, biomarkers LL-37 and neutrophils, taken individually, did not yield a significant difference in identifying healers from non-healers. However, following the teachings of the invention a combination of the two biomarkers yielded a significant predictor.

Figure 12:
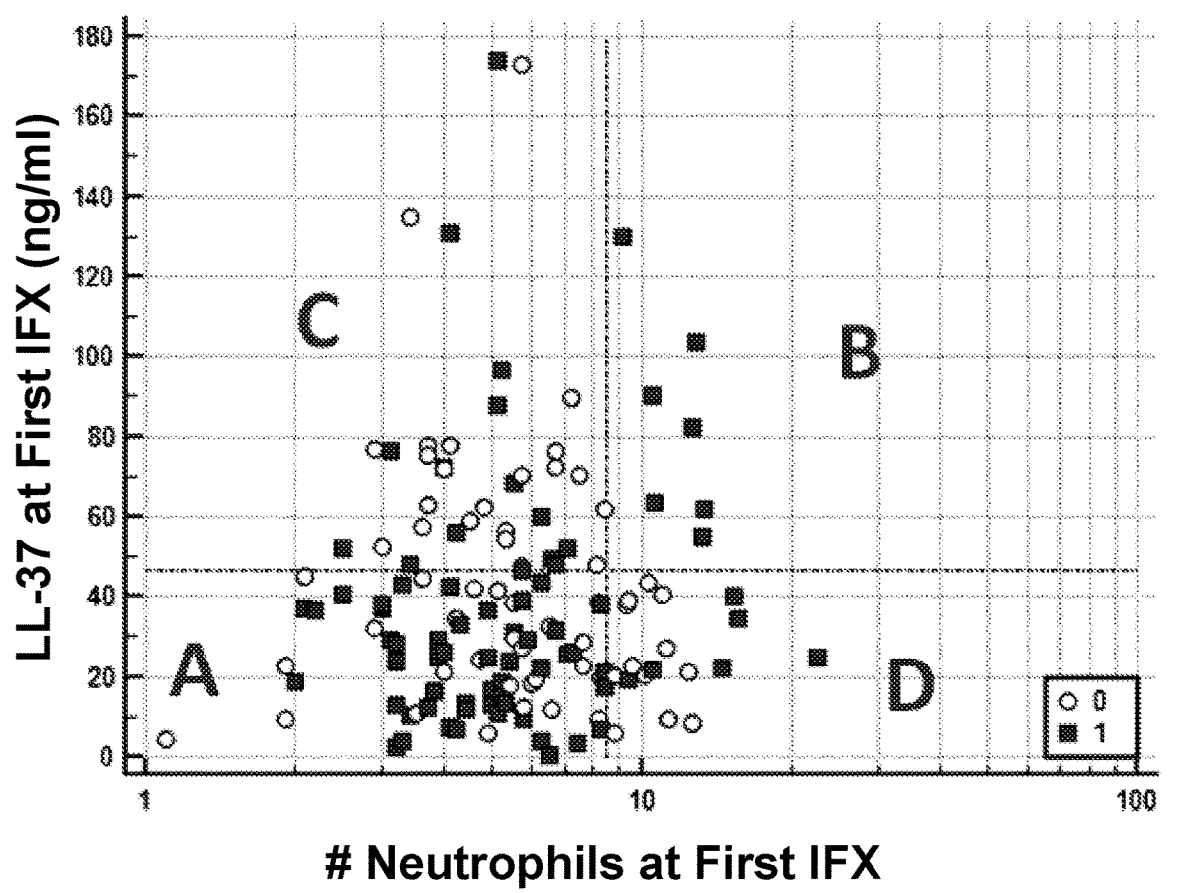
FIG. 12 is a scatter plot representing patients mucosal healing status data, as a response to treatment, in relation to their levels of LL-37 and neutrophils prior to treatment, in a study carried out in accordance with the teachings of the invention.

FIG. 12 is a scatter plot representing patients mucosal healing status data, as a response to treatment, in relation to their levels of LL-37 and neutrophils prior to treatment, in a study carried out in accordance with the teachings of the invention. In FIG. 12, each patient is represented by a mucosal healing status by a square for healers, and open circles for non-healers. In accordance with the invention, optimized cutoffs of LL-37 and neutrophils level were determined. An embodiment of the invention generated quadrants (A,B,C,D) separated at 46 ng/mL for LL-37 and 8,500/mL neutrophils. Table 7 summarizes the digitization scheme used in an embodiment of the invention.

TABLE 7

| Neutrophils × 1000/ml | LL-37 ng/ml | Assigned |
|---|---|---|
| <=8.5 | <=46 | 0 |
| >8.5 | >46 | 1 |

In this analysis, quadrants A+B was given value "1", and quadrants C+D were given value "0". While the neutrophils and LL-37 before treatment was not significant between healers and non-healers, the combination of the two resulted in a very significant difference (P=<0.001).

Figure 13:
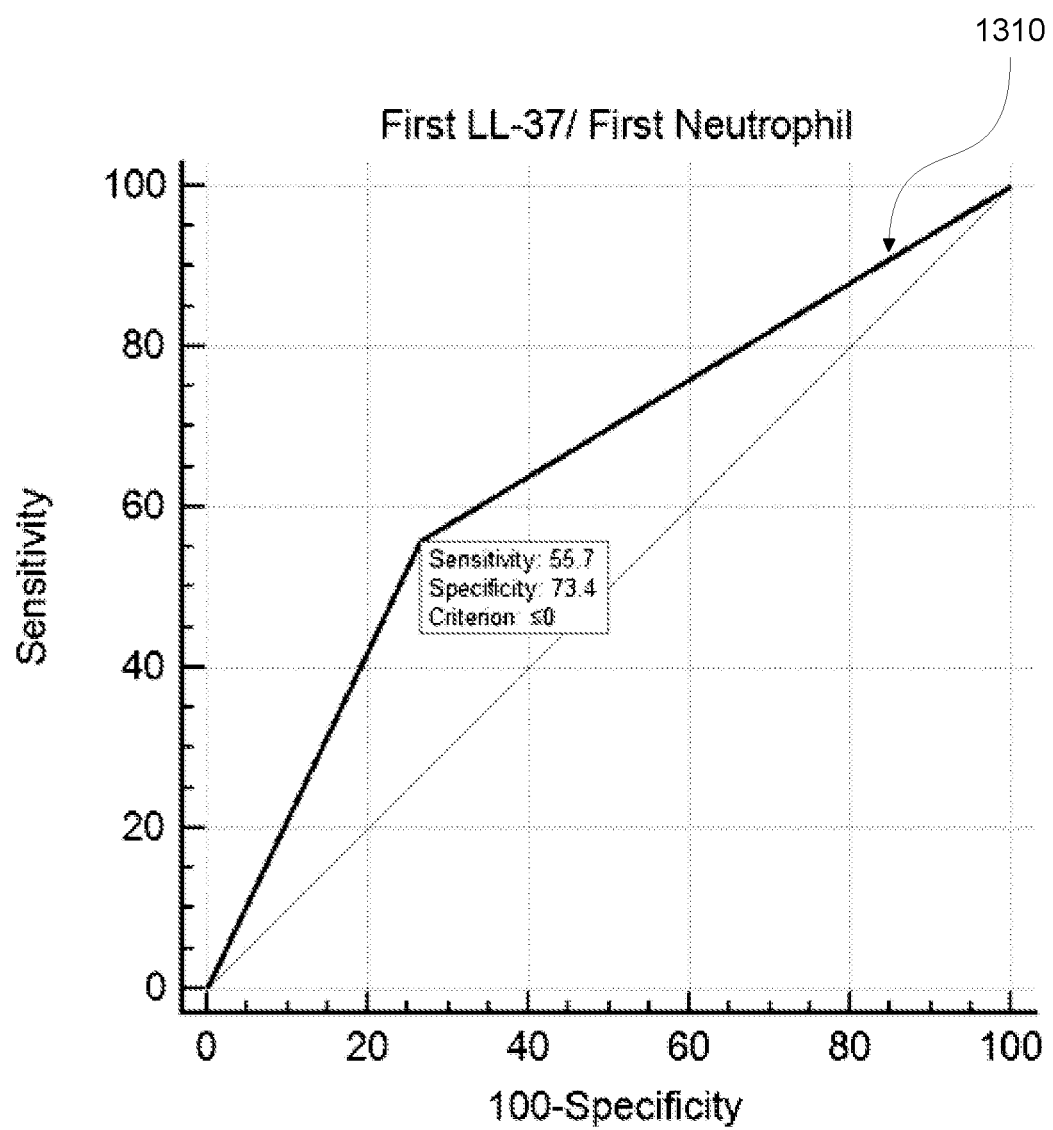
FIG. 13 is a graphical representation of the results of the Receiver Operating Characteristic (ROC) analysis for all patients under a study in accordance with embodiments of the invention.

FIG. 13 is a graphical representation of the results of the Receiver Operating Characteristic (ROC) analysis for all patients under a study in accordance with embodiments of the invention. The ROC area under the curve (AUC), delineated by line 1310, is 0.646 (64.6%).

Figure 14:
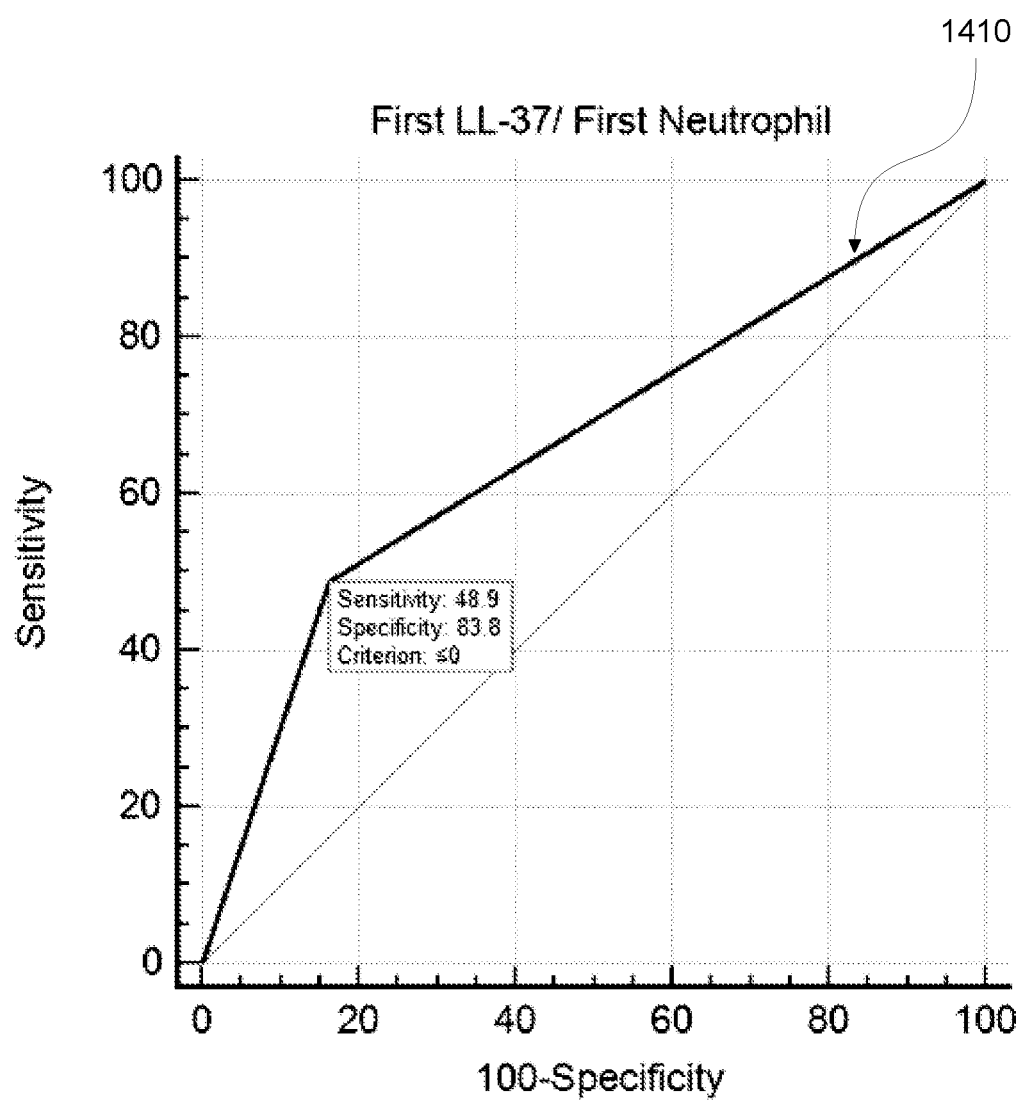
FIG. 14 is a graphical representation of the results of the Receiver Operating Characteristic (ROC) analysis for those patients under 12 weeks of treatment in accordance with embodiments of the invention.

FIG. 14 is a graphical representation of the results of the Receiver Operating Characteristic (ROC) analysis for those patients under 12 weeks of treatment in accordance with embodiments of the invention. The ROC AUC, delineated by line 1410, is 0.663 (66.3%).

Test Kit for Assessing Mucosal Healing in Human Patients

Embodiments of the invention may be implemented as a kit for measuring a panel of target biomarkers comprising LL-37, Neutrophils, CRP and CHI3L1. For example, a test kit according to the invention comprises one or more sets of antibodies specifically designed to reveal the presence and the concentration of one of the target biomarkers. Measuring a target biomarker may be carried according to the steps described above for each of LL-37, CRP and CHI3L1. A kit in accordance with the invention comprises means for determining cell counts e.g., for counting the number of neutrophils in a blood volume.

Apparatus for Assessing Mucosal Healing in Human Patients

An embodiment of the invention may be implemented in an apparatus for receiving biomarker data and providing a result indicating the status of mucosal healing in the patient from whom serum samples were taken. The apparatus may be implemented with a data input interface (e.g., an electronic reader from a blood analysis device, a computer keyboard, a storage drive a network location or any other source of biomarker data). The apparatus comprises an electronic processing unit, memory for storing data and an interface for providing an output. In particular, the apparatus is configured to execute the steps of the invention and provide an output that allows a practitioner to assess mucosal healing.

Thus a method apparatus and kit for assessing mucosal healing in a patient undergoing treatment for IBD.

What is claimed is:

1. A method for treating a human subject who has inflammatory bowel disease and suffers from no mucosal healing, the method comprising:
obtaining a weighted value of c-reactive protein (CRP) concentration in the human subject by measuring a concentration of CRP in a serum sample from a blood sample from said human subject, obtaining a discretized CRP concentration value of said concentration of CRP, wherein said discretized value of CRP concentration being zero (0) if said concentration of CRP is less than about 2.8 ng/ml, and said discretized value of CRP concentration being one (1) if said concentration of CRP is greater than about 2.8 ng/ml, multiplying said discretized CRP concentration value by a CRP coefficient of 1.12, to thus, obtain said weighted value of CRP concentration;
obtaining a weighted value of neutrophils cell count by performing a neurophil cell count in the blood sample, obtaining a discretized neurophil cell count value the discretized value of said cell count having a value zero (0) if said cell count of neutrophils is less than about 35,000 per ml, and having the value one (1) if said cell count of neutrophils is greater than about 35,000 per ml, multiplying said discretized cell count value by a cell count coefficient value of 1.6, to thus, obtain the weighted value of neurophil cell count;
obtaining a weighted value of Cathelicidin (LL-37) concentration by measuring LL-37 concentration in the serum sample, obtaining a discretized LL-37 concentration value of the measured LL-37 concentration, wherein said discretized LL-37 concentration value being zero (0) if said concentration of LL-37 is less than about 46 ng/ml, and said discretized LL-37 concentration value being one (1) if said concentration of LL-37 is greater than about 46 ng/ml, multiplying said discretized LL-37 concentration value by a LL-37 coefficient value of 0.9, to thus, obtain said weighted value of LL-37 concentration;
obtaining a weighted value of Chitinase 3-like 1 (CHI3L1) concentration in the subject by measuring a concentration of CHI3L1 in the serum sample, obtaining a discretized CHI3L1 concentration value of the measured concentration of CHI3L1, wherein said discretized CHI3L1 concentration value being zero (0) if said concentration of CHI3L1 is less than about 22 ng/ml, and said discretized CHI3L1 concentration value being one (1) if said concentration of CHI3L1 is greater than about 22 ng/ml, multiplying said discretized CHI3L1 concentration value by a CHI3L1 coefficient value of 1.1, to thus, obtain the weighted value of CHI3L1 concentration;
obtaining an index value by summing said weighted value of each of CRP concentration, the weighted value of neurophil cell count, the weighted value of LL-37 concentration and weighted value of CHI3L1 concentration, wherein said index value has an actual maximum value of 4.72;
determining that said human subject has a low mucosal healing if said index is above about 3.54; and
administering an immunosuppressant agent and/or an anti-inflammatory agent configured to treat inflammatory bowel disease and alleviate mucosal healing in the human subject.

2. The method of claim 1 further comprising alternatively measuring at least one of said concentrations of CRP, LL-37 and CHI3L1 in a blood plasma sample.

3. The method of claim 1 further comprises measuring the concentration of CRP, the concentration of LL-37 and the concentration of CHI3L1 in a blood sample from a human subject affected by Crohn's disease.

4. The method of claim 1 further comprises measuring the concentration of CRP, the concentration of LL-37 and the concentration of CHI3L1 in a blood sample from a human subject affected by Ulcerative Colitis.

5. The method of claim 1 further comprises administering a pharmaceutical composition containing an Anti-TNF($\alpha$).

6. The method of claim 1 further comprises administering a pharmaceutical composition containing an Anti-$\alpha$4$\beta$7 integrin.

7. The method of claim 1 further comprises administering a pharmaceutical composition containing an IL-23 inhibitor.

8. The method of claim 1 further comprises administering a pharmaceutical composition containing a Janus kinase (JAK) inhibitor.

9. The method of claim 1 further comprises administering a pharmaceutical composition containing an S1P1-receptor and S1P5-receptor modulator.

10. The method of claim 1 further comprises administering a pharmaceutical composition containing an aminosalicylates.

11. The method of claim 1 further comprises administering a pharmaceutical composition containing Corticosteroids.

12. The method of claim 1 further comprises monitoring mucosal healing level by repeatedly obtaining said index value from said human subject and further comprises adjusting a dose of said immunosuppressant agent and/or an anti-inflammatory agent.

13. A system for non-invasively determining mucosal healing in a human subject undergoing treatment for inflammatory bowel disease using a set of biomarkers, the system comprising:
a blood sample collection kit for collecting a blood sample from said human subject;
an assay reagent for measuring a concentration of c-reactive protein (CRP) in said blood sample;
a cell count system for producing a cell count of neutrophils in said blood sample;
an assay reagent for measuring a concentration of Human type of Cathelicidin (LL-37) in said blood sample;
an assay reagent for measuring a concentration of Chitinase 3-like 1 (CHI3L1) in said blood sample; and
a computer system configured to obtain data pertaining to said concentration of CRP, said a cell count of neutrophils, said concentration of LL-37 and said concentration of CHI3L1, and having an interface to produce an output for use by a practitioner assessing mucosal healing in response to treatment, said computer system is configured with program code, when executed, is configured to cause said computer system to:
generate a weighted value of CRP concentration;
generate a weighted value of neutrophils cell count;
generate a weighted value of said LL-37 concentration;
generate a weighted value of CHI3L1 concentration;
generate an index value by summing said weighted value of CRP concentration, said weighted value of neutrophils cell count, said weighted value of said LL-37 concentration and said weighted value of CHI3L1 concentration, said index value ranges between zero (0) and a computed maximum value; and
determine that said human subject has a low mucosal healing if said index value is within the upper quarter of said computed maximum value.

14. The system as in claim 13 further comprises said Index value ranges from zero (0) to ten (10).

15. The system as in claim 13 further comprises said Index value ranges from zero (0) to one hundred (100).

16. The system as in claim 13 further comprises a blood sample collection kit from a human subject affected by Ulcerative Colitis, further comprising an assay reagent for measuring a concentration of CRP in said blood sample, an assay reagent for measuring a concentration of LL-37 in said blood sample, an assay reagent for measuring a concentration of CHI3L1 in said blood sample, and wherein said computer system further comprises computer program code configured to cause said computer system to:
generate a discretized CRP concentration value of said concentration of CRP, wherein said discretized value of CRP having a value zero (0) if said concentration of CRP is less than about 2.8 ng/ml, and a value one (1) if said concentration of CRP is greater than about 2.8 ng/ml, and obtaining said weighted value of CRP concentration by multiplying said discretized CRP concentration value by a CRP coefficient;
generate a discretized cell count value of said cell count of neutrophils, wherein said discretized value of said cell count having a value zero (0) if said cell count of neutrophils is less than about 35,000 per ml, and having the value one (1) if said cell count of neutrophils is greater than about 35,000 per ml, and obtaining said weighted value of said neutrophils cell count by multiplying said discretized cell count value by a cell count coefficient;
generate a discretized LL-37 concentration value, wherein said discretized LL-37 concentration value having a value zero (0) if said concentration of LL-37 is less than about 46 ng/ml, and a value one (1) if said concentration of LL-37 is greater than about 46 ng/ml, and obtaining said weighted value of said LL-37 concentration by multiplying said discretized LL-37 concentration value by a LL-37 coefficient; and
generate a discretized CHI3L1 concentration value, wherein said discretized CHI3L1 concentration value having value "0" if said concentration of CHI3L1 is less than about 22 ng/ml, and having a value one (1) if said concentration of CHI3L1 is greater than about 22 ng/ml, and obtaining said weighted value of said CHI3L1 concentration by multiplying said discretized CHI3L1 concentration value by a CHI3L1 coefficient.

17. The system as in claim 16, wherein said computer system further comprising computer program code configured to cause said computer to:
assign a value 1.12 to said CRP coefficient;
assign a value 1.6 to said cell count coefficient;
assign a value 0.9 to said LL-37 coefficient; and
assign a value 1.1 to said CHI3L1 coefficient.

* * * * *